US 8,272,262 B2
Sep. 25, 2012

(12) United States Patent
Cabrera et al.

(10) Patent No.: US 8,272,262 B2
(45) Date of Patent: Sep. 25, 2012

(54) UNDERWATER SENSOR APPARATUS

(75) Inventors: Ramon Cabrera, Miami, FL (US);
Zhivko Grozev, San Diego, CA (US);
Alexander Kovachev, San Diego, CA (US); Daryl B. Slocum, La Mesa, CA (US); Adam Jackson, San Diego, CA (US); Daniel Osiecki, Asheville, NC (US)

(73) Assignee: YSI Incorporated, Yellow Springs, OH (US)

( * ) Notice: Subject to any disclaimer, the term of this patent is extended or adjusted under 35 U.S.C. 154(b) by 0 days.

(21) Appl. No.: 13/041,046

(22) Filed: Mar. 4, 2011

(65) Prior Publication Data

US 2011/0214500 A1  Sep. 8, 2011

Related U.S. Application Data

(60) Provisional application No. 61/311,230, filed on Mar. 5, 2010.

(51) Int. Cl.
*G01C 13/00* (2006.01)
(52) U.S. Cl. .................................. 73/170.29; 73/170.33
(58) Field of Classification Search ... 73/170.29–170.33
See application file for complete search history.

(56) References Cited

U.S. PATENT DOCUMENTS

| 4,122,428 A | 10/1978 | Morrow, Jr. |
| 5,200,706 A | 4/1993 | Yada |
| 5,578,751 A * | 11/1996 | French .................. 73/170.29 |
| 5,821,405 A * | 10/1998 | Dickey et al. ............. 73/53.01 |
| 6,111,249 A * | 8/2000 | Garner, III ................. 250/239 |
| 6,536,272 B1 * | 3/2003 | Houston et al. ........... 73/170.29 |
| 7,343,261 B1 * | 3/2008 | Kell ............................. 702/127 |
| 7,380,435 B1 * | 6/2008 | Henderson et al. ......... 73/12.01 |
| 7,380,453 B1 * | 6/2008 | Van Every et al. ........ 73/170.29 |
| 7,832,295 B2 * | 11/2010 | Rodriguez et al. ........... 73/866.5 |
| 8,048,372 B1 * | 11/2011 | Cheung et al. ................ 422/52 |
| 2004/0042341 A1 | 3/2004 | Tenghamm |
| 2010/0005857 A1 * | 1/2010 | Zhang et al. ................ 73/29.02 |

FOREIGN PATENT DOCUMENTS

| JP | 0623752 B | 3/1994 |
| JP | 09-043004 A | 2/1997 |

OTHER PUBLICATIONS

International Search Report from related PCT International Application No. PCT/US2011/027244.

* cited by examiner

*Primary Examiner* — Andre Allen
(74) *Attorney, Agent, or Firm* — Peter K. Hahn; Pillsbury Winthrop Shaw Pittman LLP

(57) ABSTRACT

An underwater sensor device comprises a submersible housing including one or more housing components, one or more sensors for monitoring and collecting water characteristics, a controller for controlling operations of the one or more sensors and an graphical user interface mounted to the housing that displays the water environmental data. The housing defines a channel that extends through one of the housing components, and at least one of the sensors is mounted to the housing and extends into the channel. The controller is disposed within the housing and is operatively connected to the one or more sensors.

20 Claims, 21 Drawing Sheets

UNDERWATER SENSOR APPARATUS

CROSS REFERENCE TO RELATED APPLICATIONS

This application claims priority to U.S. Patent Application Ser. No. 61/311,230, filed Mar. 5, 2010, which is hereby incorporated by reference in its entirety.

BACKGROUND

There are numerous indicia of water phenomena that are of value to oceanographers, hydrologists and surveyors as well as to the captain and crew of surface or subsurface vessels. For example, water temperature, depth, conductivity, salinity, sound speed, optical properties, nutrient availability, etc., may provide valuable information for a number of divergent uses. This information may be used to expand the knowledge base of ocean parameters in general, or may be useful in navigation, sonar communication and the like.

Historically, data collection has been completed using instruments lowered from ships, or moored instrument arrays which must be recovered. The cost of operating a manned vessel on the high seas often is prohibitive. Moreover, vessel availability cannot always be assured. Oceanographic experiments are thus constrained in many cases by factors other than the phenomenon which is intended for study.

There are numerous apparatus available to measure various ocean parameters. One common apparatus consists of a set of small probes attached to a large metal rosette wheel. The rosette is lowered on a cable down to the seafloor, and the water properties are observed via a conducting cable connecting the apparatus to a remotely operated computer. In other systems instruments are lowered into the water on a cable and data is recorded on an on-board data recorder. The data is then transferred to another computer for review and analysis. However, these and other known apparatus have many disadvantages. Most existing devices require extra equipment such as a separate computer or other device to review data along with other connectors and cables to connect the sensor apparatus to the computer. Another common disadvantage is a delay in seeing the collected data because downloading and processing data can be complicated and time consuming. Many existing underwater sensor apparatus are cumbersome to handle and deploy and may require a special winch for handling. In addition, existing underwater sensor apparatus require the user to take field notes for every cast and retrieval point to record position, time and date of each deployment.

SUMMARY

It is an object of embodiments of the disclosure to provide an underwater sensor apparatus with a built in display, or graphical user interface, that allows data entry, review and download from the apparatus without the need for a separate computer.

It is another object of embodiments of the disclosure to provide an underwater sensor apparatus having global positioning system (GPS) capability incorporated therein to automatically record position, time and date information.

It is an object of embodiments of the disclosure to provide an underwater sensor apparatus having a transceiver, or more particularly bluetooth capability, incorporated therein to transmit data collected by the apparatus.

It is another object of embodiments of the disclosure to provide an underwater sensor apparatus having weighting for directional stability and control.

It is an object of embodiments of the disclosure to provide an underwater sensor apparatus having a small size such that the apparatus can be held in the user's hand, can fit in the user's pocket or be easily tied to a fishing line.

It is another object of embodiments of the disclosure to provide an underwater sensor apparatus having sensors with rapid response capability so the apparatus can collect high resolution data while being rapidly submerged.

It is an object of embodiments of the disclosure to provide an underwater sensor apparatus having sensors located within a channel to protect the sensors from damage.

It is another object of embodiments of the disclosure to provide an underwater sensor apparatus having a channel and sensors located within the channel to eliminate the need for a pumping system to facilitate water flow on the sensors.

It is an object of embodiments of the disclosure to provide an underwater sensor apparatus having magnetic switches to power the system on and off and for user inputs in the field.

It is another object of embodiments of the disclosure to provide an underwater sensor apparatus that is easily castable.

Exemplary embodiments comprise a system of monitoring and collecting water environmental data comprising a submersible housing, one or more sensors mounted to the housing, a controller disposed within the housing, a graphical user interface mounted to the housing, a GPS receiver disposed within the housing and a transceiver disposed within the housing. The submersible housing defines a channel extending therethrough oriented such that water flows through the channel when the system is submerged and moving through the water. The channel may have a first end and a second end, and each end may be substantially funnel-shaped. In exemplary embodiments, the channel may define one or more access points, and one or more of the sensors may extend into the channel through the access points. A pressure cal module may operatively connect the one or more sensors to the submersible housing.

The controller is operatively connected to the one or more sensors and controls their operations. In exemplary embodiments, the sensors include one or more of: a temperature sensor, a conductivity electrode and a pressure sensor. The one or more sensors collect selected water environmental data, and the graphical user interface displays the water environmental data. An interface module may provide an electrical interconnection between the sensors and the graphical user interface. The transceiver sends the water environmental data to a remote data collection system. The GPS collects geographical data and sends at least some of the geographical data through the transceiver to a remote data collection system.

In exemplary embodiments, the submersible housing comprises two housing components, with the channel defined in the second housing component. The first housing component may house the graphical user interface, and the second housing component may house the one or more sensors. The system may further comprise a weighted endcap component fixedly attached to the submersible housing at a bottom portion thereof. Exemplary embodiments include a jacket to cover and protect the submersible housing. A stylus may be provided along with one or more magnetic switches activated by the stylus.

Exemplary embodiments of a sensor apparatus comprise a submersible housing including a first and second housing component, an endcap component fixedly attached to the one or more housing components at a bottom portion thereof, one or more sensors mounted to the second housing component, an display mounted to the first housing component and an interface module located between the one or more sensors and the display.

The second housing component defines a channel extending therethrough, and the channel is oriented substantially perpendicular to a surface of water in which the apparatus is submerged. The endcap component may be weighted to maintain the sensor apparatus in an orientation substantially perpendicular to the surface of water. In exemplary embodiments, the channel defines one or more access points, and the one or more sensors may extend into the channel through the access points. The one or more sensors monitor and collect water environmental data, and the display displays the water environmental data. An interface module located between the one or more sensors and the display electrically connects the one or more sensors to the display.

The sensor apparatus may further comprise a controller disposed within the housing and operatively connected to the one or more sensors. The controller controls operations of the one or more sensors. Exemplary embodiments also include a GPS receiver disposed within the housing and adapted to collect geographical data. The sensor apparatus may also comprise a transceiver disposed within the housing, and the transceiver sends the water environmental data to a remote data collection system.

Exemplary embodiments of an underwater sensor device comprise a submersible housing including one or more housing components and defining a channel that extends through one of the housing components, one or more sensors for monitoring and collecting water environmental data, at least one of the sensors being mounted to the housing and extending into the channel, a controller for controlling operations of the one or more sensors, the controller being disposed within the housing and operatively connected to the one or more sensors, and an graphical user interface mounted to the housing that displays the water environmental data.

DETAILED DESCRIPTION

Figure 1:
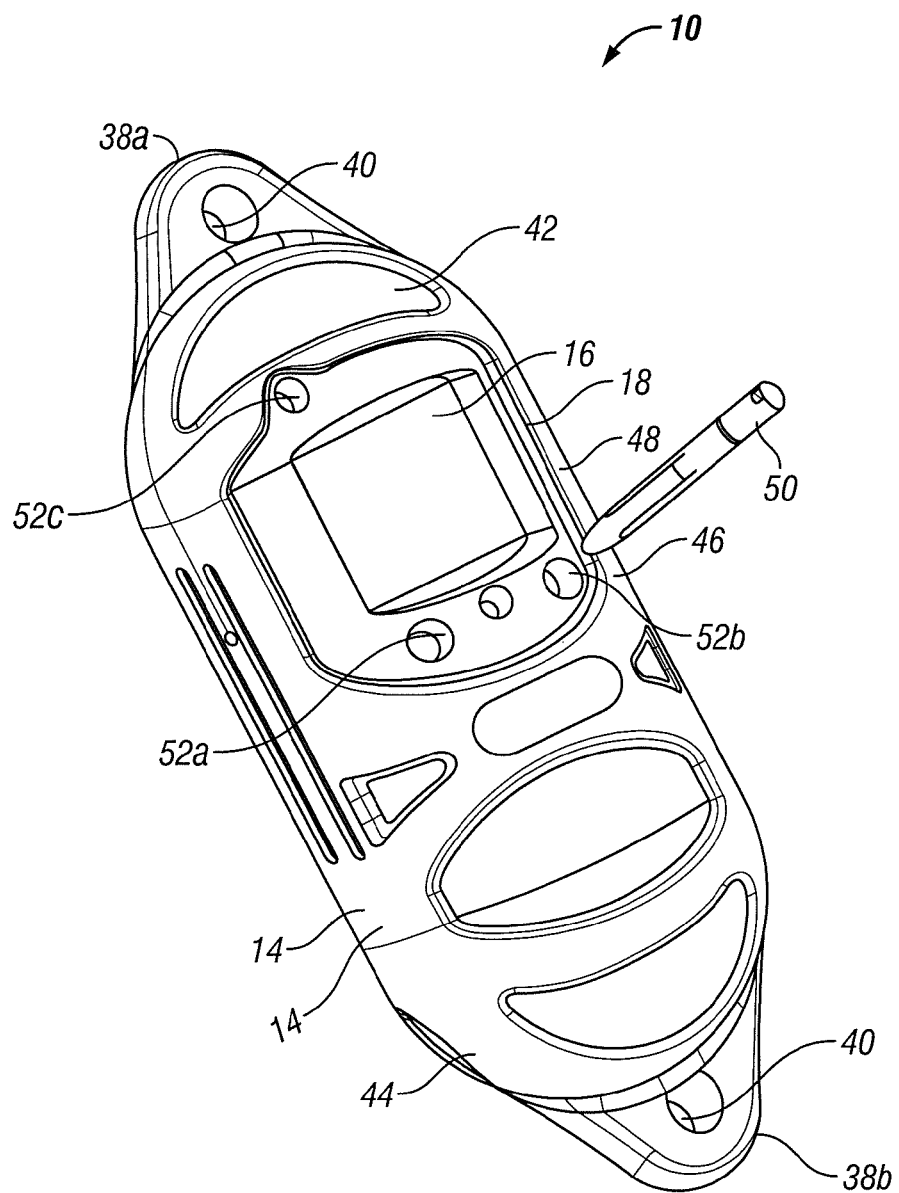
FIG. 1 is a perspective view of an embodiment of an underwater sensor apparatus in accordance with the present disclosure.
Figure 2:
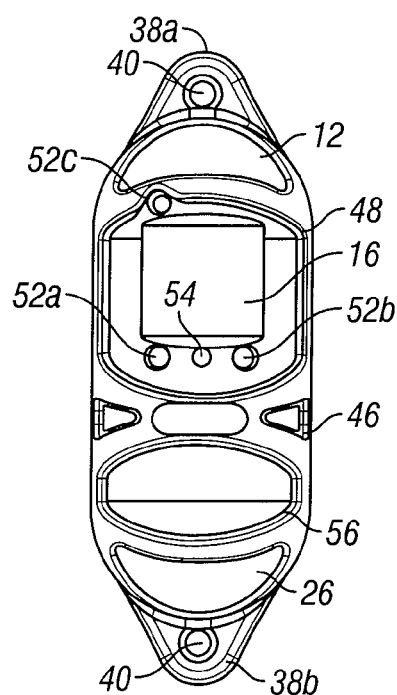
FIG. 2 is a front view of an embodiment of an underwater sensor apparatus in accordance with the present disclosure.
Figure 3:
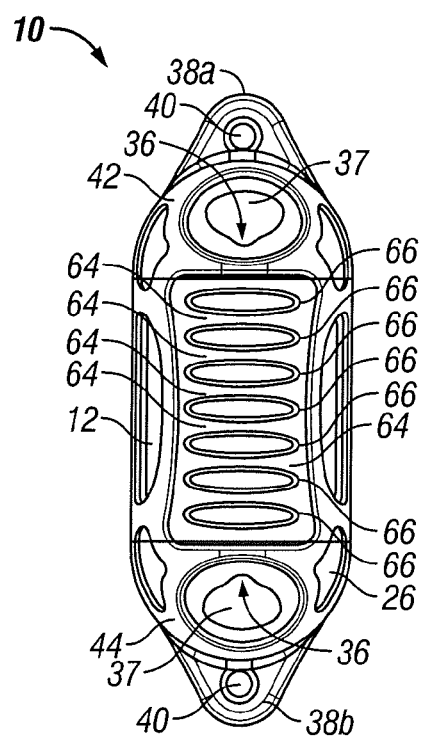
FIG. 3 is a rear view of an embodiment of an underwater sensor apparatus in accordance with the present disclosure.
Figure 4:
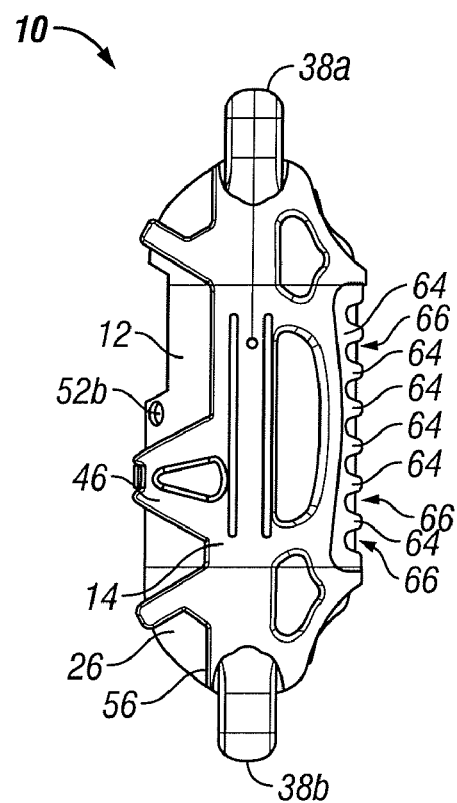
FIG. 4 is a side view of an embodiment of an underwater sensor apparatus in accordance with the present disclosure.
Figure 5:
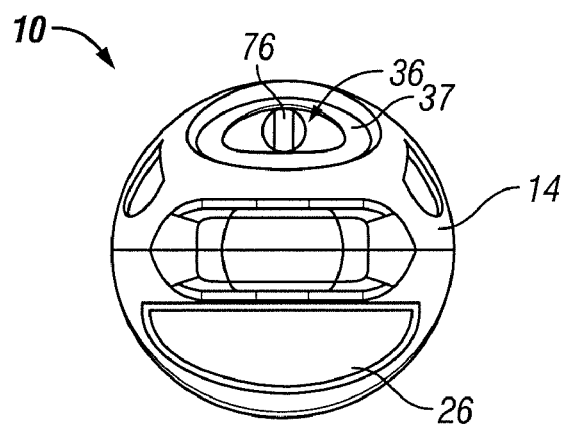
FIG. 5 is a bottom view of an embodiment of an underwater sensor apparatus in accordance with the present disclosure.

In the following paragraphs, embodiments of the disclosure will be described in detail by way of example with reference to the attached drawings. Throughout this description, the exemplary embodiments and examples shown should be considered as exemplars, rather than as limitations on embodiments of the disclosure. As used herein, the "embodiments," "exemplary embodiments" or "embodiments of the disclosure" refer to any one of the embodiments described herein, and any equivalents. Furthermore, reference to various feature(s) of the "embodiments," "exemplary embodiments or "embodiments of the disclosure" throughout this document does not mean that all claimed embodiments or methods must include the referenced feature(s).

Referring first to FIGS. 1-8, exemplary embodiments of an underwater sensor apparatus will be described. Underwater sensor apparatus 10 comprises two housing components 12a, 12b and jacket 14. A first housing component 12a houses the display 16 and includes window 22 to allow visual access to the display or graphical user interface 16 by the user of the apparatus. display 16 may be a liquid crystal display (LCD) or may use other suitable display technologies. A stylus 50 may be provided for user to interact with the display 16 through the use of magnetic switches 52a, 52b, 52c included inside the housing. The housing further includes a recess for each switch to minimize the chance of an unintended activation of a switch. This is accomplished by mounting the magnetic switch adjacent to the bottom of a recess. To activate the switch, the magnetic stylus is inserted into the recess. These switches or buttons may be waterproof so they are protected from water damage. As described in more detail herein, stylus 50 is used to activate magnetic switches 52 to input data, activate a system activity, activate a screen or otherwise navigate the display 16. LED 54 emits light to signal, e.g., that the apparatus's power is on. A second housing component 12b is configured to house one or more sensors and/or probes used to collect and measure various underwater parameters, which will be described in more detail herein.

Figure 6:
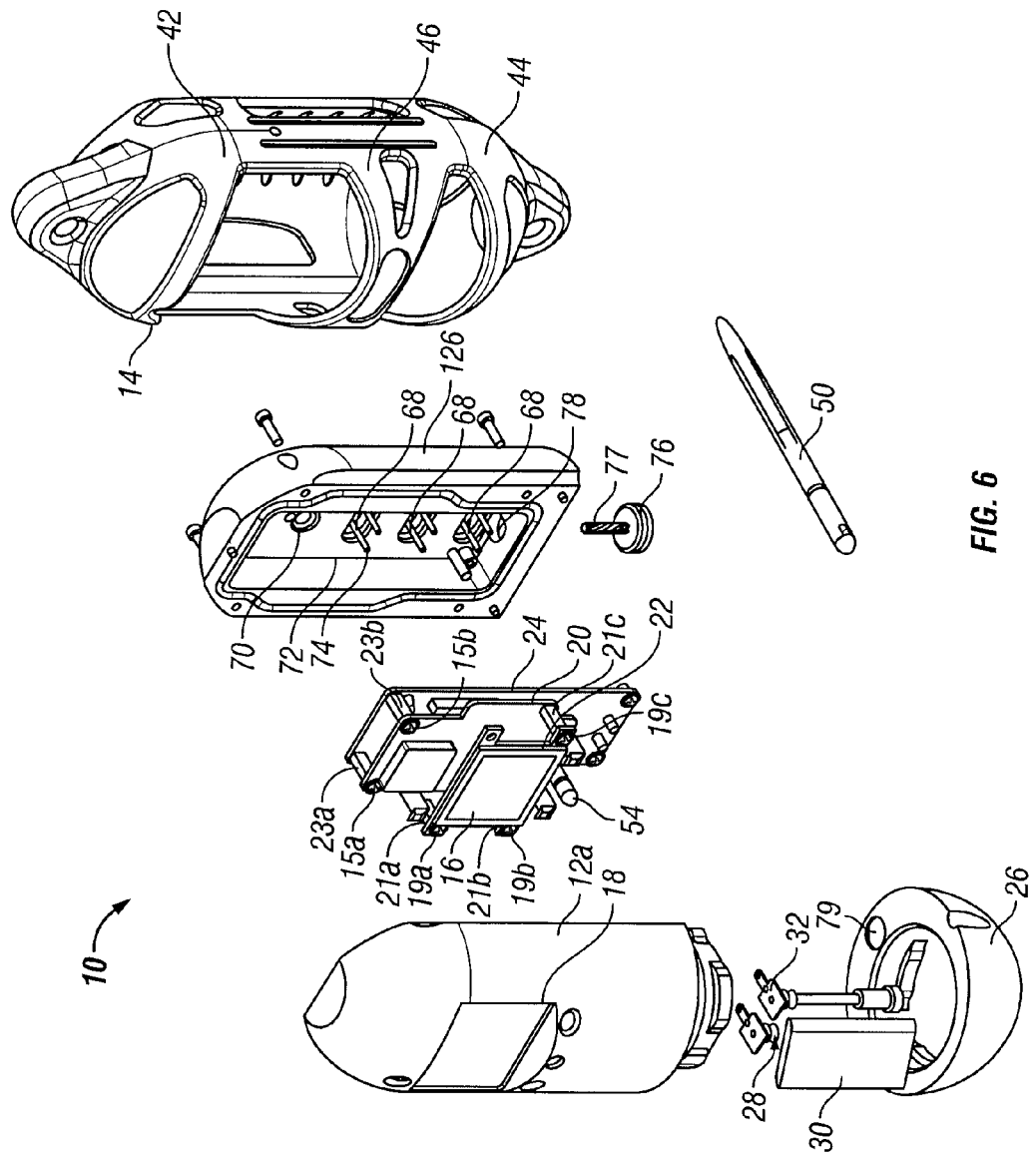
FIG. 6 is an exploded view of an embodiment of an underwater sensor apparatus in accordance with the present disclosure.
Figure 7:
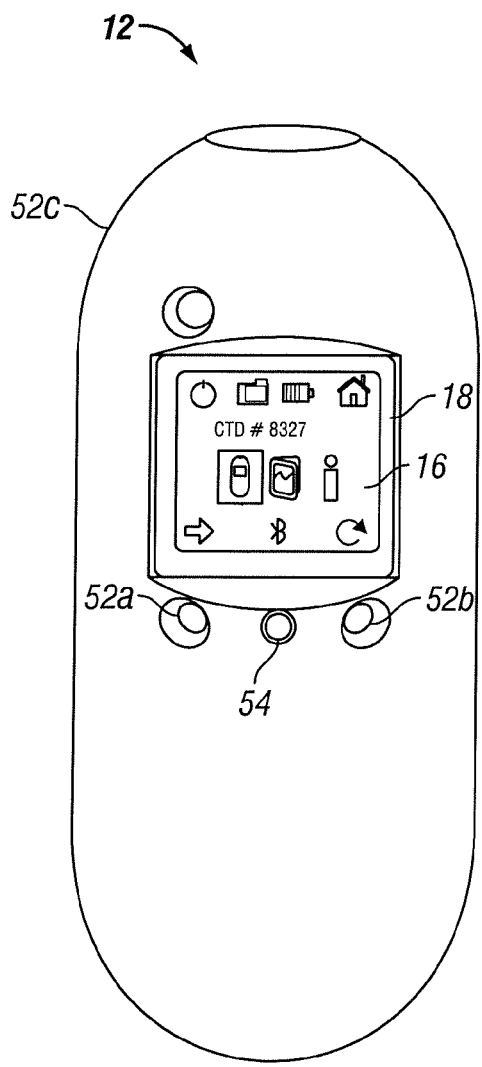
FIG. 7 is a front view of an embodiment of an underwater sensor apparatus in accordance with the present disclosure
Figure 8:
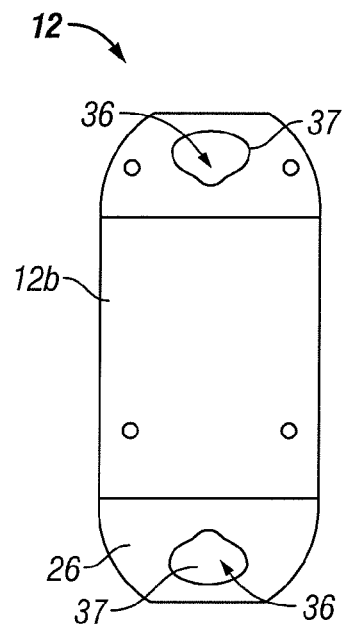
FIG. 8 is a rear view of an embodiment of an underwater sensor apparatus in accordance with the present disclosure.

As best seen in FIG. 6, an interface module 20 stands between display 16 and sensor board 24 and provides both a structural and electrical interconnection between the sensors and/or probes located within housing component 12b and the display located within housing component 12a. More particularly, graphical user interface or display 16 is fastened to interface module 20 using screws 19a-19c threaded through standoffs 21a-21c. Interface module 20 is, in turn, fastened to sensor board 24 via screws 15a, 15b threaded through standoffs 23a, 23b. First housing component 12a and second housing component 12b are attached by fastener assemblies including screws and O-rings 17, 18 with the display 16, interface module 20 and various sensors and/or probes securely held and sealed within the housing components 12a, 12b.

Endcap component 26 is a substantially hollow rounded end piece that connects to both housing components 12a, 12b by a screw and socket mechanism 28. Endcap component 26 also serves as an enclosure for battery 30 and contains battery contact 32. In exemplary embodiments, the underwater sensor apparatus 10 is powered by two double AA batteries, which can be loaded and replaced without the use of tools. Endcap component 26 may be weighted to provide directional stability and control, making the underwater sensor apparatus 10 easier and faster to deploy. Weighting may be accomplished by adding weight to the endcap end of the unit such that the device descends endcap end first. The batteries located in the endcap component 26 can provide such weighting.

The second housing component 12b defines a channel 36 that extends substantially vertically through the back of the component. Each end of the channel may have a funnel-shaped portion 37. Channel 36 contains the access points 68 for at least some of the apparatus's sensors and probes so that these components are protected from damage. Channel 36 has a self-flushing design that acts as a natural pump to provide the advantage of facilitating water flow on the apparatus' sensors and probes for improved data collection. The weight distribution of housing components 12a, 12b ensures that the underwater sensor apparatus 10 falls vertically when being submerged and maintains a vertical orientation when being pulled up out of the water. In this manner, as the device moves through the water, the amount of water flowing through the channel is increased for both data collection passes and for flushing purposes. More particularly, as the apparatus moves either up or down through the water, the water is constantly pushed through channel 36. Thus, new water is constantly replacing water at the level of each sensor so the sensors get data readings at every water level. This ensures accurate data readings, particularly for the temperature sensor 70, which needs a constant rate of water flow to measure temperature accurately. It should be noted that the vertical orientation allows the user to measure the rate of fall by monitoring changes in pressure. Thus, the user can use flow measurements to correct problems relating to water flow rate that may occur with the temperature sensor 70.

The fully assembled housing components 12a, 12b and endcap component 26 fit snugly within jacket 14, which serves to protect the housing and endcap components and the electronics and hardware therein. Jacket 14 may have any formation suitable to provide adequate protection for the housing 12 and the components therein, and an exemplary configuration will now be described. Jacket 14 comprises top and bottom attachment portions 38a, 38b, and each attachment portion defines an aperture 40 suitable for threading and securing attachment mechanisms such as chain links or cable. The front section of jacket 14 includes a rounded top shell portion 42, a rounded bottom shell portion 44 and middle cross portion 46 to provide extra protection and support. Top shell portion 42 covers the top front of housing component 12a, and bottom shell portion 44 covers the bottom front of housing component 12b. Between top shell portion 42 and middle cross portion 46, jacket 14 defines a first cutout 48 sized and shaped to allow the user easy access to magnetic switches 52a, 52b and viewing of display 16. Jacket 14 defines a second cutout 56 between middle cross portion 46 and bottom shell portion 44. The back of jacket 14 defines a top and bottom cutout 60a, 60b sized to expose the top and bottom openings of channel 36. Center portion 62 of the back of the jacket 14 defines a series of alternating lateral strips 64 and cutouts 66. This arrangement of strips 64 and cutouts 66 provides additional stability and support for housing component 12b.

Referring to FIG. 6, some of the internal components of underwater sensor apparatus 10 will now be described. It should be noted that placement of the sensors and probes can vary considerably and provide many forms of data including but not limited to pressure, temperature, conductivity, depth, salinity, sound speed, dissolved oxygen, turbidity, chlorophyll, pH, nitrates, nitrites, carbon dioxide, water velocity, acoustic backscattering strength, fluorescence and water velocity. It should be noted that the embodiments discussed herein show exemplary configurations and many other arrangements are possible. The sensor apparatus 10 comprises temperature sensor 70, which is disposed in housing component 12b and extends into channel 36 through an access point 68 so that it can measure the temperature of the water when submerged. Temperature sensor 70 may be of any suitable type, e.g., a thermistor, which is one of the most accurate types of temperature sensors. A thermistor is an element composed of a material that exhibits a large change in resistance proportional to a small change in temperature. Thermistors usually have negative temperature coefficients, which means the resistance of the thermistor decreases as the temperature increases.

Also disposed within housing component 12b are conductivity electrodes 74 and pressure sensor 20. In exemplary embodiments, conductivity electrodes are made of titanium to provide more robust conductivity, but they may be made of any suitable conductive material. Pressure cal module 72 is a circuit board that facilitates operative connection of sensors to the underwater sensor apparatus 10 without the need for additional wires. The pressure cal module 72 may be mounted flush to the housing, and wires from the sensors may soldered to the pressure cal module. The pressure cal module may contain pads to support some calibration resistors that are specific to the installed pressure sensor, and then passes the conditioned signals on to the main circuit board via a connector (not shown). Thus, housing components 12a, 12 can be manufactured separately and more cheaply because pressure cal module 72 facilitates their operational interconnection.

In an exemplary configuration, conductivity electrodes 74 are located below the temperature sensor 70. The conductivity electrodes 74 extend out of housing component 12b into channel 36 through access points 68 so that they can measure the conductivity when submerged. Pressure sensor 76 is disposed within the bottom of housing component 12b and plugs hole 78. Wires 77 extend through the hole 78 into housing component 12b and are connected to pressure cal module 72. The pressure sensor 76 is exposed to water via a hole (not shown) in the right inner side of channel 36, so that pressure sensor 76 can make pressure readings. The underwater sensor apparatus also contains a central processing unit (CPU) 80, or controller, on which software is run to process the collected data. The CPU may be any form of controller or microprocessor.

In operation, the user prepares the underwater sensor apparatus 10 for a cast by using the stylus 50, which may be a magnetic stylus having a magnetic tip, to program the apparatus to collect the desired water characteristics. These characteristics could include temperature, pressure, conductivity and depth, among others. The user first turns the underwater sensor apparatus 10 on by activating one of the magnetic switches 52a, 52b, 52c with the stylus 50. LED 54 will emit light to indicate that the apparatus is on. Next, the user again activates one of the magnetic switches 52a, 52b with the stylus 50 to select the "Cast" icon on the display 16, which may be waterproof. It should be noted that the magnetic stylus 50 and magnetic switches 52 may be used for any kind of data input and for navigating various screens on the display 16. Magnetic switches are advantageous because they have no moving parts, can be used both in and out of the water and rarely fail in the field.

Figure 12:
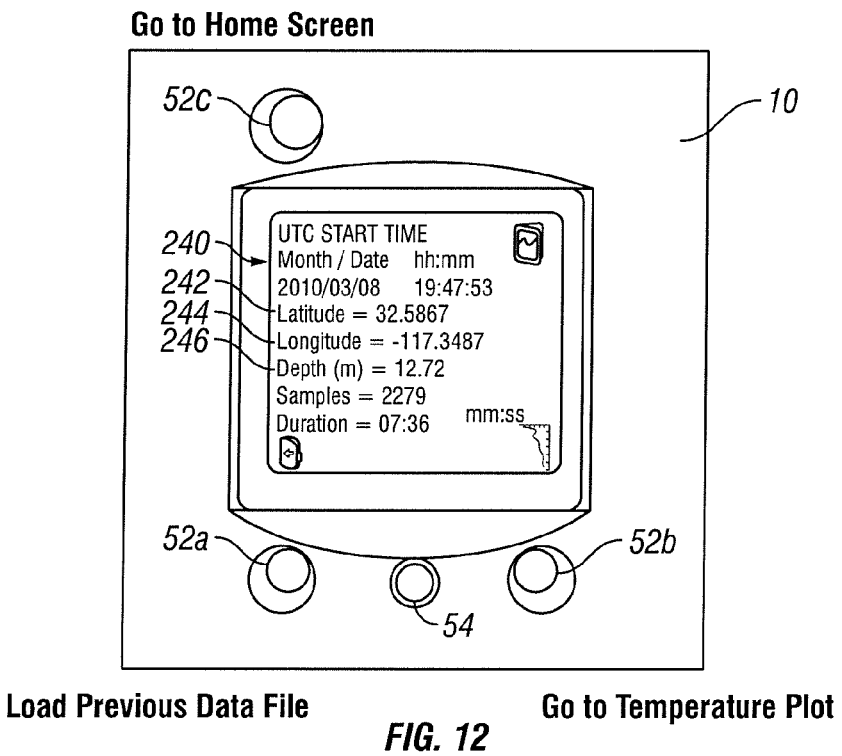
FIG. 12 is a detail view of an embodiment of an underwater sensor apparatus in accordance with the present disclosure showing an display screen.
Figure 13:
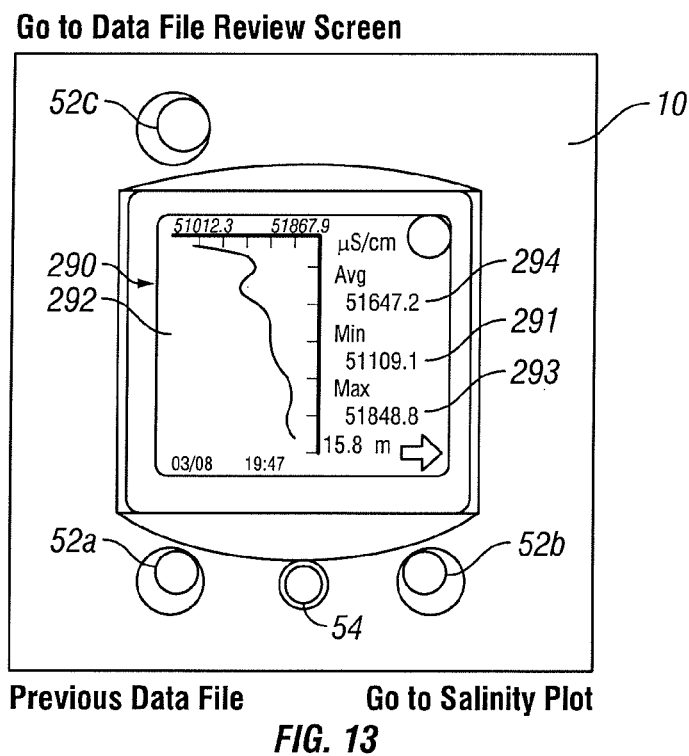
FIG. 13 is a detail view of an embodiment of an underwater sensor apparatus in accordance with the present disclosure showing an display screen.

The GPS 110 automatically provides the user with geographic data, including the exact position, date and time of the cast via the display 16. Finally, the user selects the icon for starting data collection and lowers the underwater sensor apparatus 10 into the water. This may be done by securing attachment mechanisms such as chain links or cable to aperture 40 of top attachment portion 38a of the apparatus jacket 14. After attaching the cable or line, the device is lowered into the water. Typically the device is allowed to free-fall, although it is possible to control the descent speed by controlling the deployment of the line or cable. The device is allowed to descend to a predetermined depth or to the bottom depending on the test parameters. Once the bottom or desired depth is reached the device is retrieved by reeling in the line or cable. Once the underwater sensor apparatus 10 is out of the water the user can view the data on the display 16, as best seen in FIGS. 12 and 13, or wirelessly download the data to a computer. Alternatively, the underwater sensor apparatus 10 could include a waterproof computer connector port like a USB or mini-USB connector port.

Referring to FIGS. 6 and 14A-C, the layout and operation of the underwater sensor apparatus 10 will be described in more detail. It can be seen that pressure sensor 20 and temperature sensor or thermistor probe 70 are operatively connected to pressure cal module 72, which, in turn, is operatively connected to sensor board 82. The sensor board 82 is operatively connected to interface board 84, which, in turn, is operatively connected to display 16. Battery 30 is connected to interface board 84 via battery contact 32. Interface board comprises GPS capability 110 and transceiver 112 to provide bluetooth capability. The bluetooth capability eliminates the need for various connectors and cables to start, program, review or download data. LED 54 is also located on interface board 84. Sensor board 82 comprises power supply 86, which provides power to CPU 80, recorder 88 and PI filter 92 to prevent supply noise from affecting the system.

CPU 80 comprises analog-to-digital converter (ADC) 94 and digital-to-analog converter (DAC) 96. The CPU 80 controls de-bug port 90 and receives data from pressure circuit 98 and temperature circuit 100 upon those components receiving pressure and temperature data from pressure sensor 20 and temperature probe 70, respectively. DAC 96 conducts waveform conditioning 102 and conductivity drive and scale selection 104. Conductivity electrodes 74 feed data into sensor board 82, which conducts signal selection 106 and signal amplification and conditioning 108 before feeding the conductivity data to ADC 94 in CPU 80. Voltage references 114 are provided to the temperature circuit 100 and the pressure circuit 98 and are used to conduct signal amplification and conditioning 108. Waveform conditioning 102, conductivity drive and scale selection 104, signal selection 106 and signal amplification and conditioning 108 are performed by conductivity block or circuit 116. The waveform or frequency output may be arbitrary and could comprise sine waves. Several frequency simulations could be used and could be modulated to reduce capacitance. The conductivity block also measures current and phase information. One possible configuration of conductivity block is the six circuit design, as best seen in FIG. 14.

After the underwater sensor apparatus 10 boots up 2000, it reads the configuration parameters 2002 that are entered in by the user and computes DAC output waveforms 2004. The underwater sensor apparatus 10 then waits for the user to indicate the start of data acquisition mode 2006. Upon receiving the instruction to start data acquisition, the underwater sensor apparatus 10 effects several steps to prepare for data acquisition. These steps 2008 include calibrating analog-to-digital (ADC) converters, setting up and running data acquisition timers, setting initial resistor range and starting DAC waveform output. The sample accumulators may be reset 2010, and the underwater sensor apparatus 10 will check the acquired data readings to determine if they correlate to the user requested readings in an average interval 2012. If the average interval is complete, the underwater sensor apparatus 10 will check if there are any accumulated readings 2026.

If at least one reading is accumulated, the sample mean temperature, pressure, conductivity A and conductivity B will be calculated. At this stage, the underwater sensor apparatus 10 will also compute the mean for all other requested parameters for diagnostic purposes and may collect sample statistics as well. If there are no accumulated readings, a bad sample will be generated 2028. The next steps 2032 may include recording either the accumulated reading or the bad sample to an internal recorder, outputting the sample on the display 16 and/or transmitting the sample via the underwater sensor apparatus's bluetooth capability. The underwater sensor apparatus 10 will then determine if the user requested to end sampling 2034 and, if so, will complete data acquisition. If the user has not requested to end sampling, the underwater sensor apparatus 10 will continue data acquisition by reverting to step 2010 and reset sample accumulators.

If, after step 2012, the averaging interval is not complete, the underwater sensor apparatus 10 will read more samples from temperature sensor 70, conductivity electrode 74, pressure sensors 20, 76 and a range resistor and store the sampled values in ADC counts 2014. One or more of the parameters temperature, pressure, phaseA, resistanceA, conductivityA, phaseB, resistanceB and conductivityB may be computed 2016. The underwater sensor apparatus 10 will then check the readings to determine if the measurements were done in the requested range 2018. If they were done correctly, the last reading will be accumulated 2020. If they were done in the wrong range, a new range will be selected, the DAC waveform will be re-programmed and the range resistors may be switched. Then the underwater sensor apparatus 10 will revert to step 2012 and again determine whether the acquired readings correspond to the requested readings.

Figure 14A:
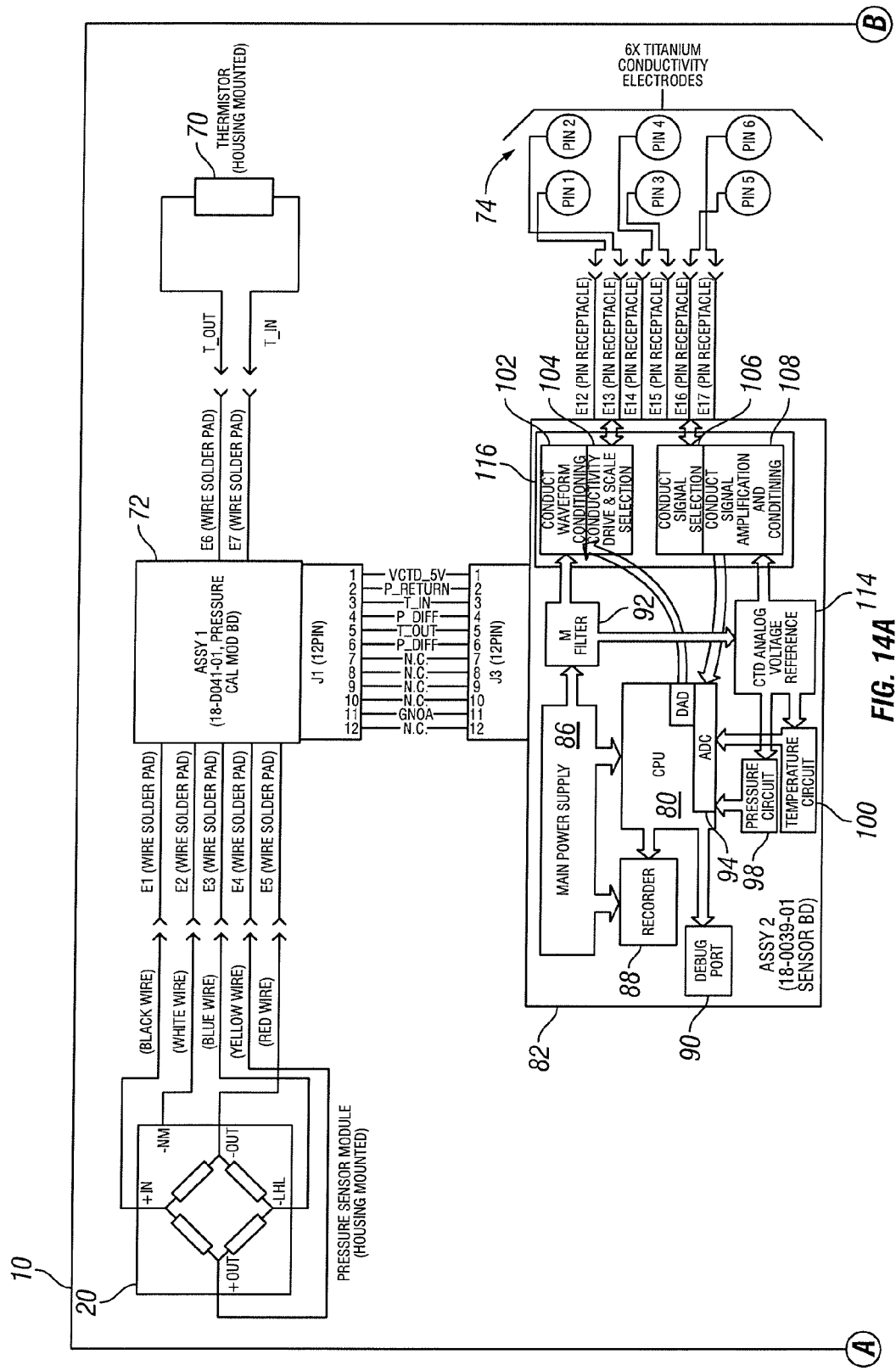
FIG. 14A is part one of a schematic diagram of an embodiment of an underwater sensor apparatus in accordance with the present disclosure.
Figure 14B:
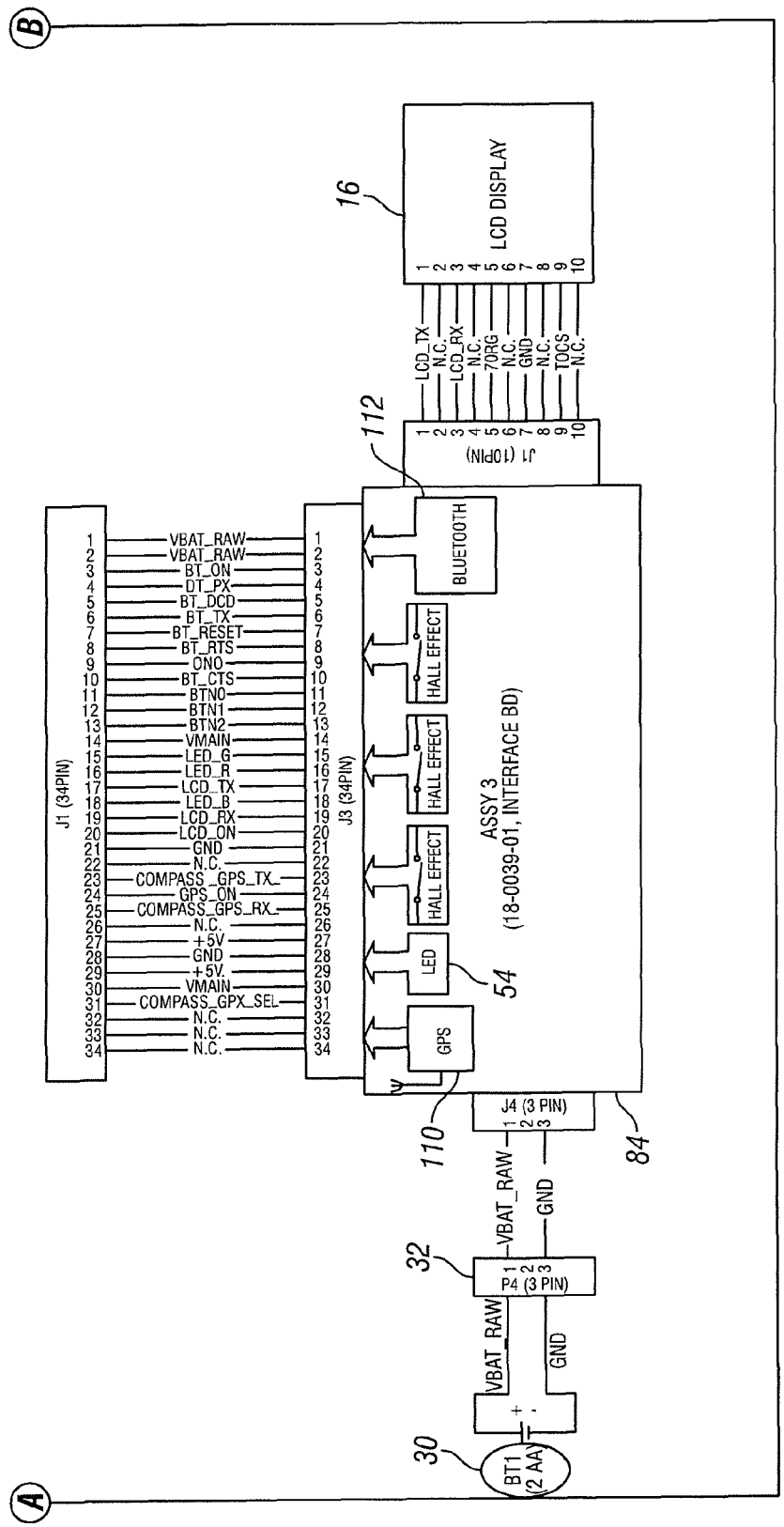
FIG. 14B is part two of a schematic diagram of an embodiment of an underwater sensor apparatus in accordance with the present disclosure.
Figure 15A:
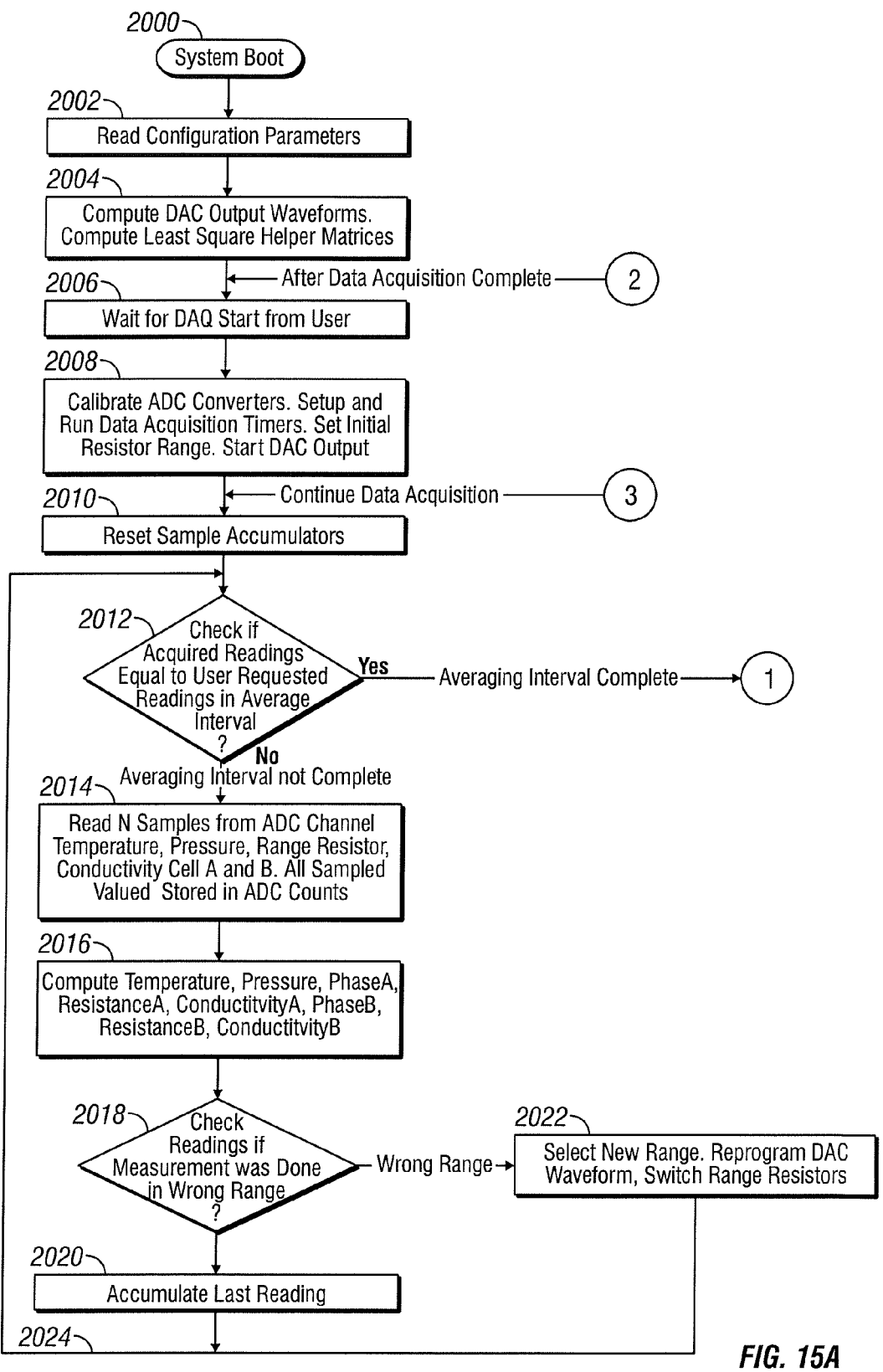
FIG. 15A is part one of a flow chart showing operation of an embodiment of an underwater sensor apparatus in accordance with the present disclosure.
Figure 15B:
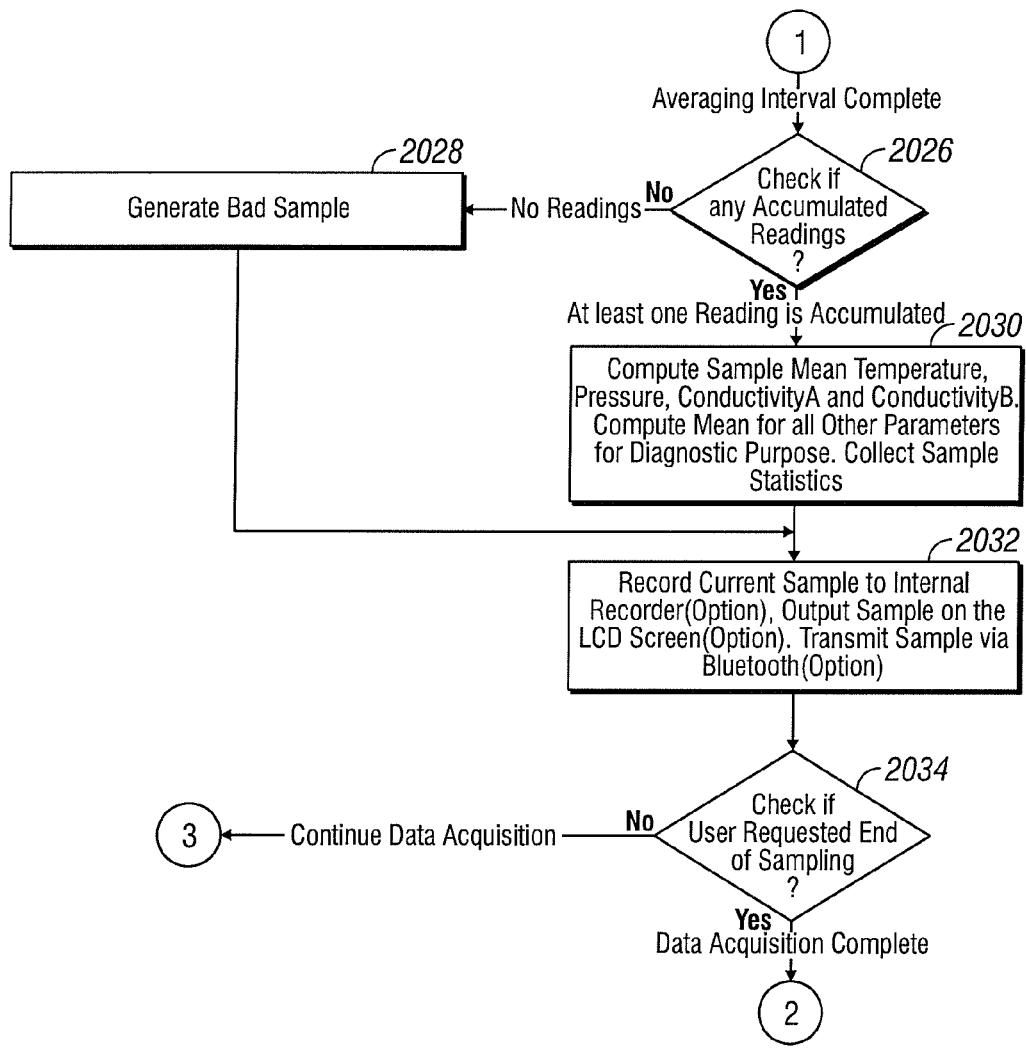
FIG. 15B is part two of a flow chart showing operation of an embodiment of an underwater sensor apparatus in accordance with the present disclosure.
Figure 16A:
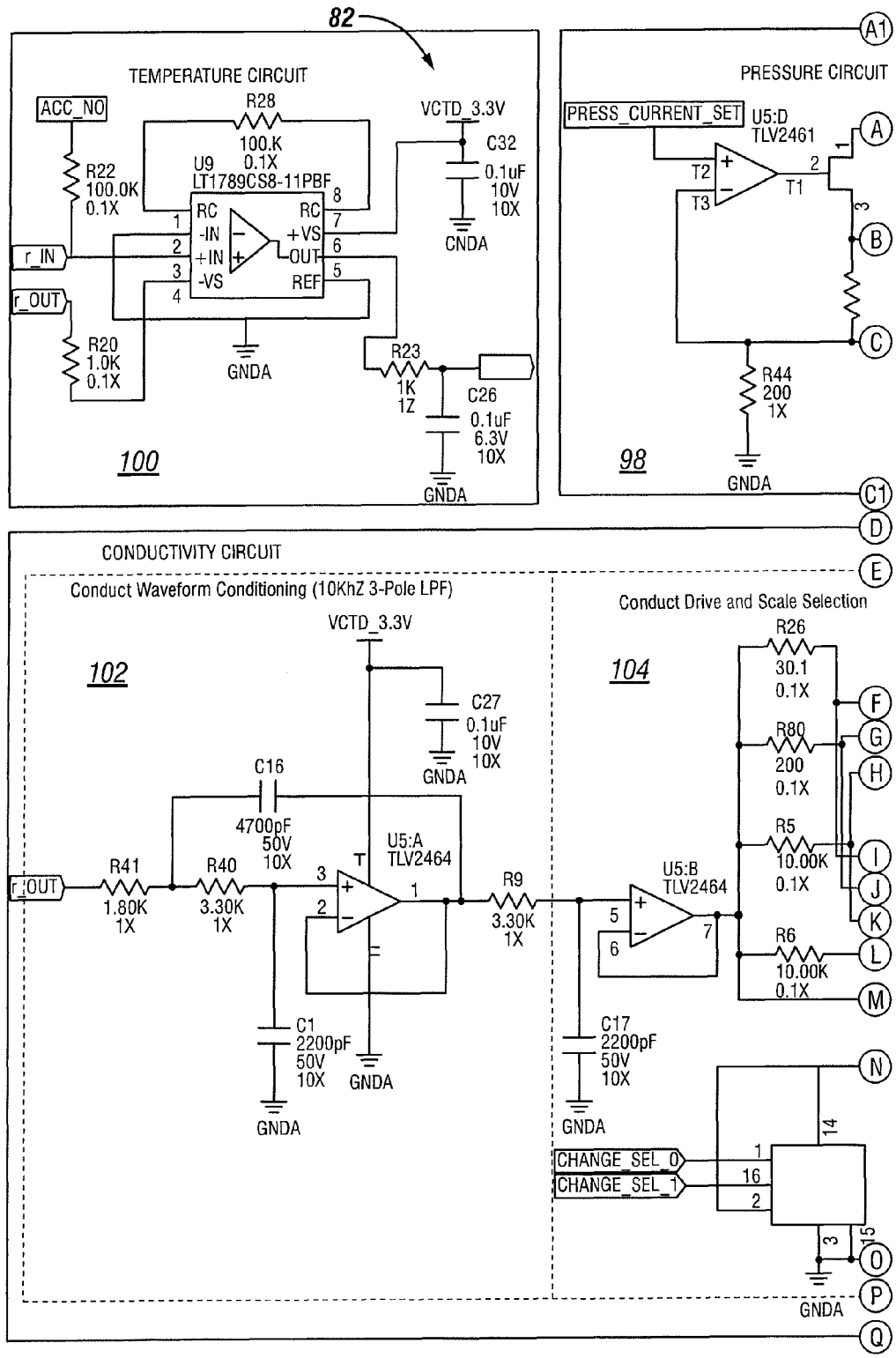
FIG. 16A is part one of a circuit diagram of a portion of a sensor board of an embodiment of an underwater sensor apparatus in accordance with the present disclosure.
Figure 16B:
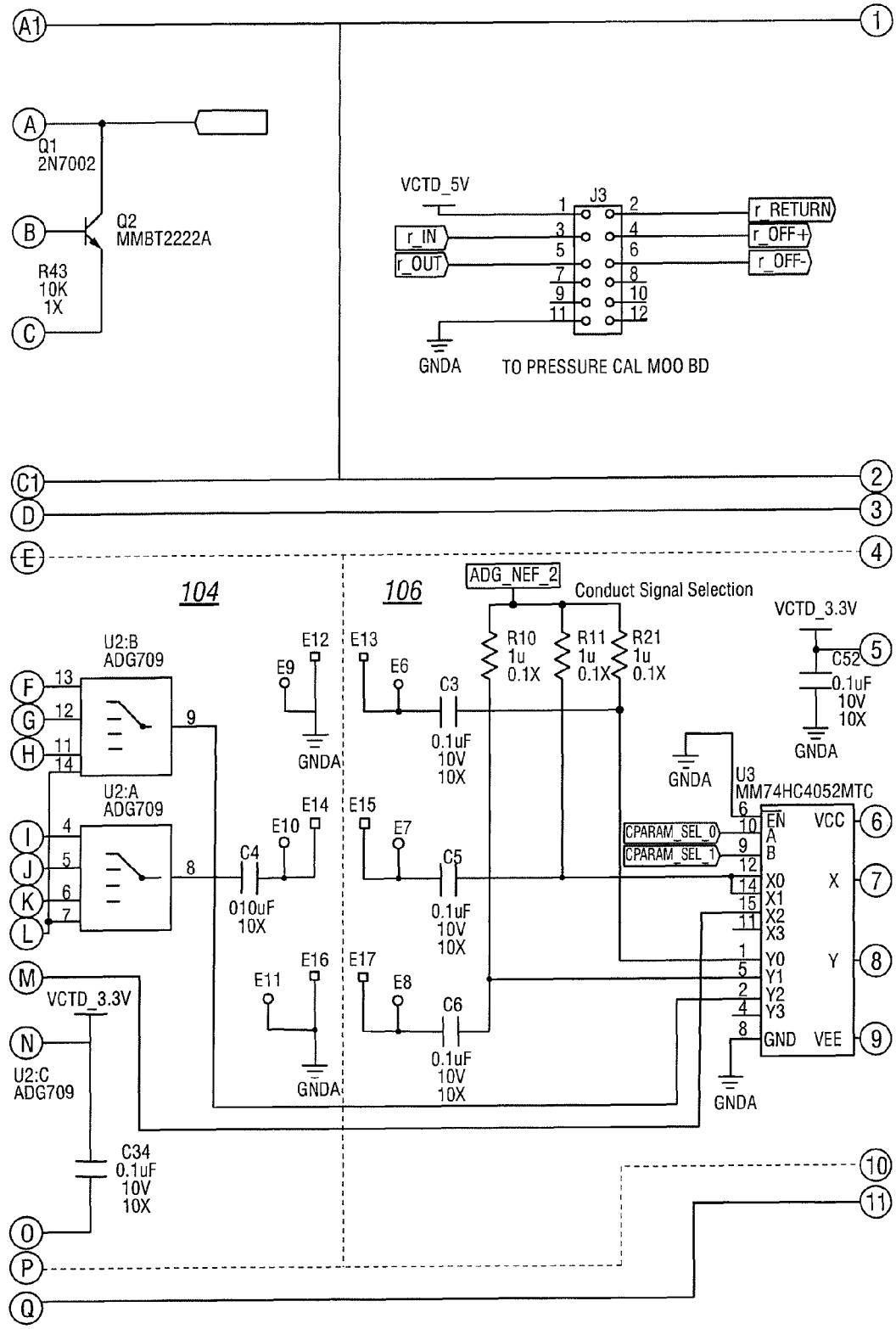
FIG. 16B is part two of a circuit diagram of a portion of a sensor board of an embodiment of an underwater sensor apparatus in accordance with the present disclosure.
Figure 16C:
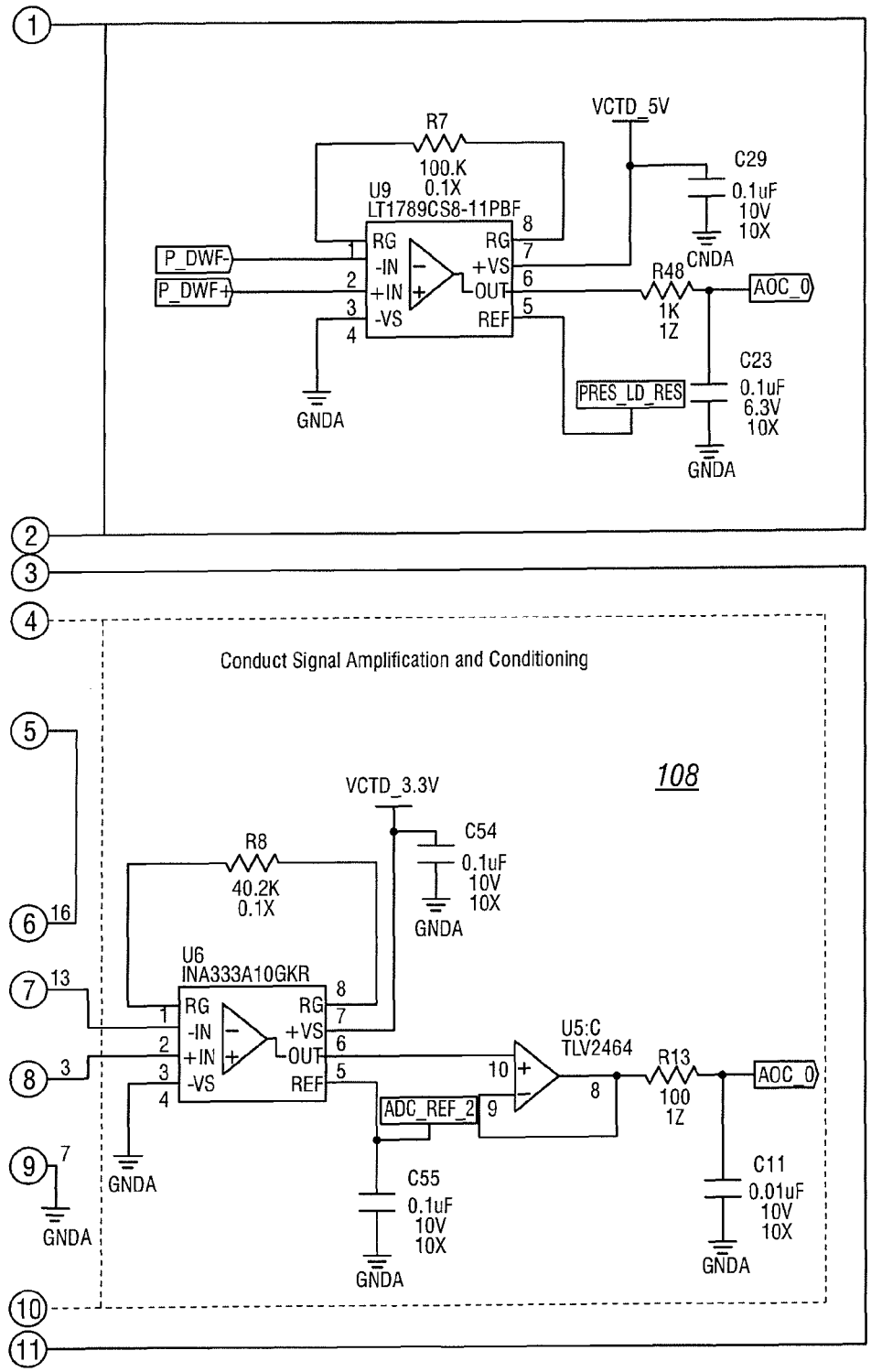
FIG. 16C is part three of a circuit diagram of a portion of a sensor board of an embodiment of an underwater sensor apparatus in accordance with the present disclosure.
Figure 17A:
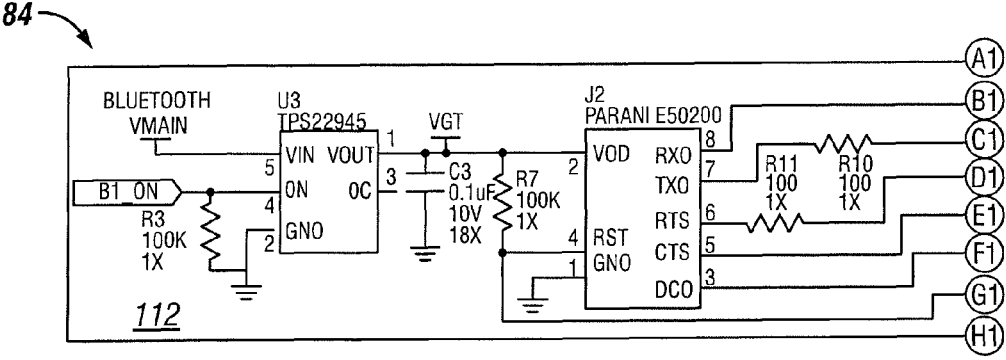
FIG. 17A is part one of a circuit diagram of an interface board of an embodiment of an underwater sensor apparatus in accordance with the present disclosure.
Figure 17A:
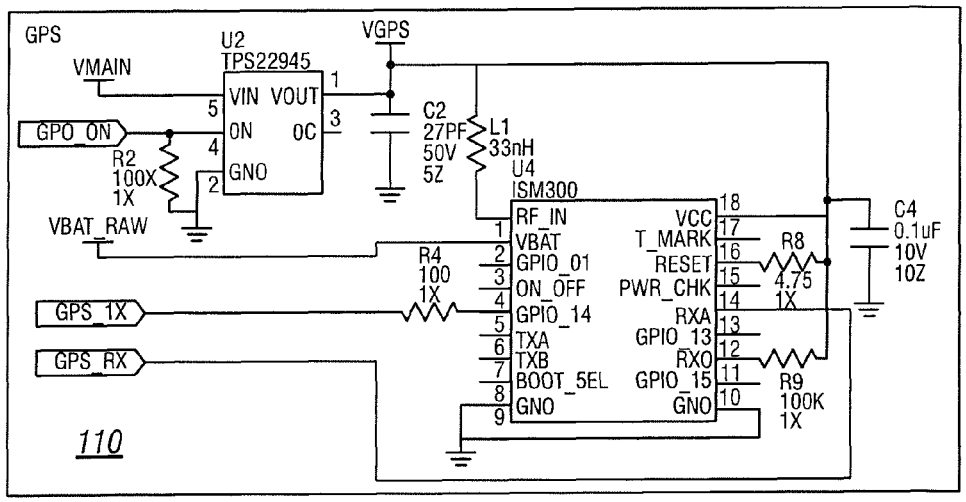
Figure 17A:
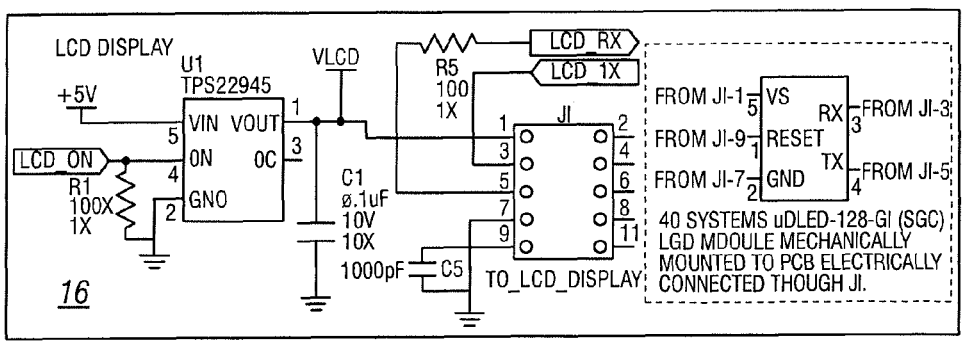
Figure 17A:
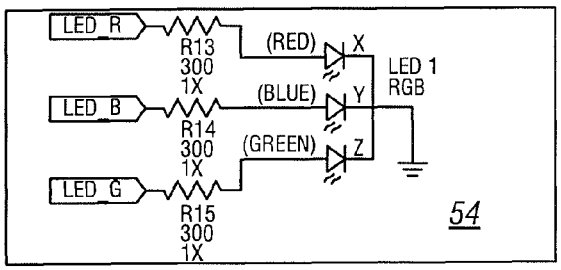
Figure 17B:
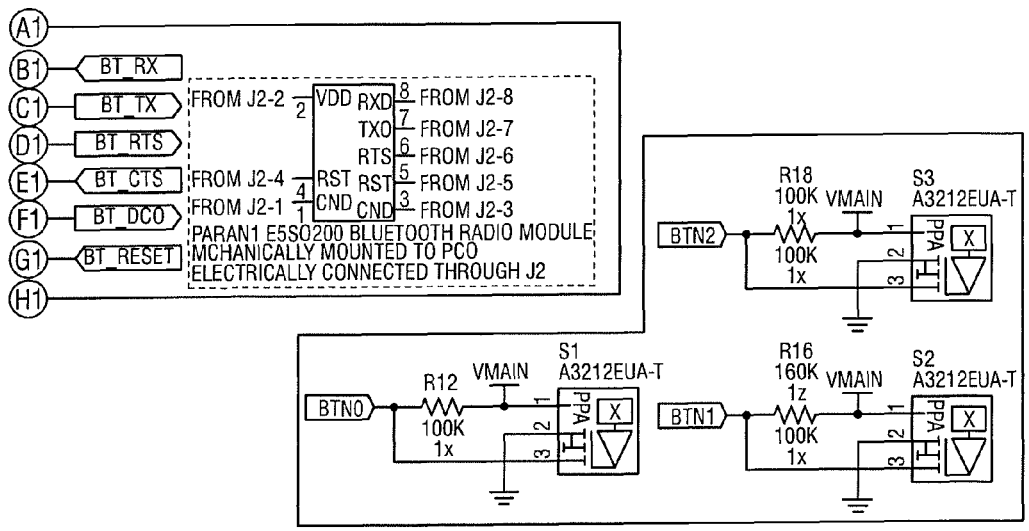
FIG. 17B is part two of a circuit diagram of an interface board of an embodiment of an underwater sensor apparatus in accordance with the present disclosure.
Figure 17B:
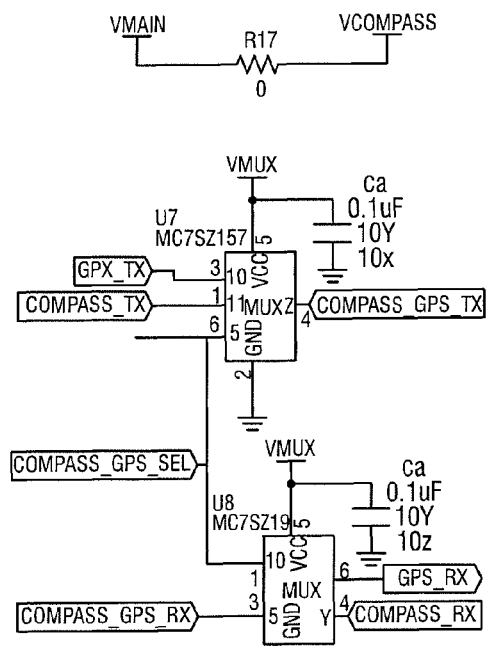
Figure 17C:
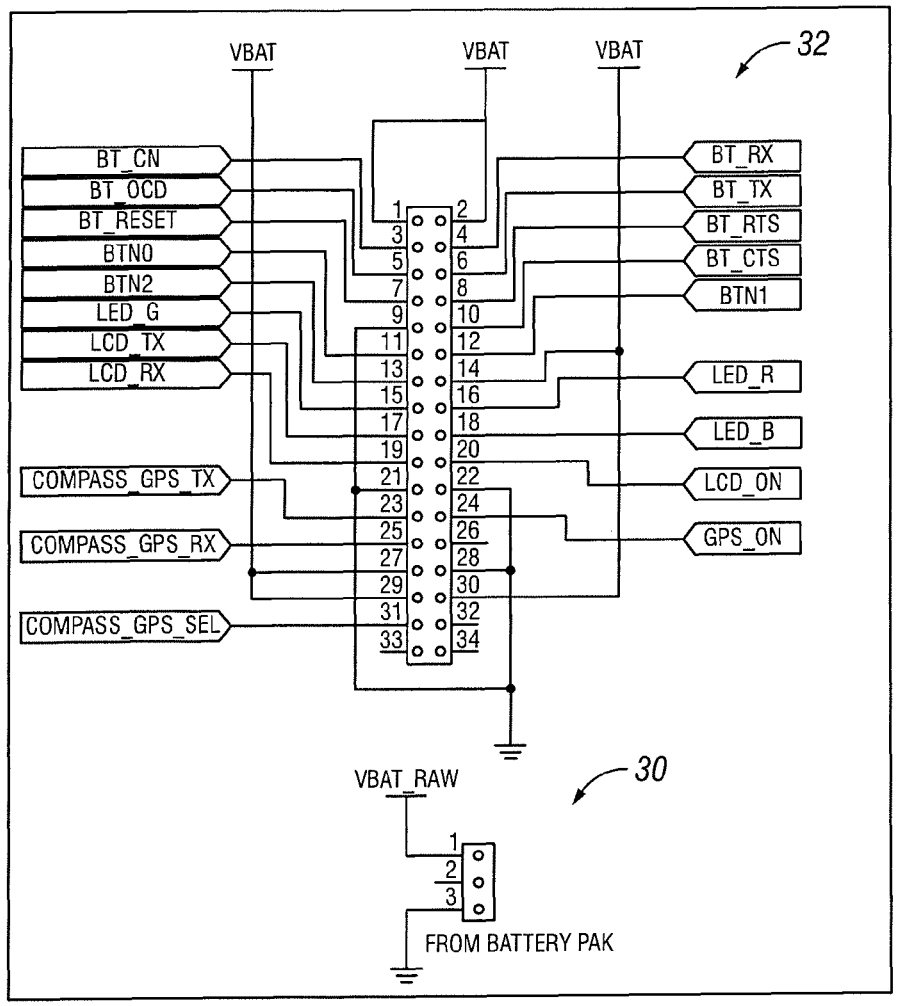
FIG. 17C is part three of a circuit diagram of an interface board of an embodiment of an underwater sensor apparatus in accordance with the present disclosure.
Figure 17C:
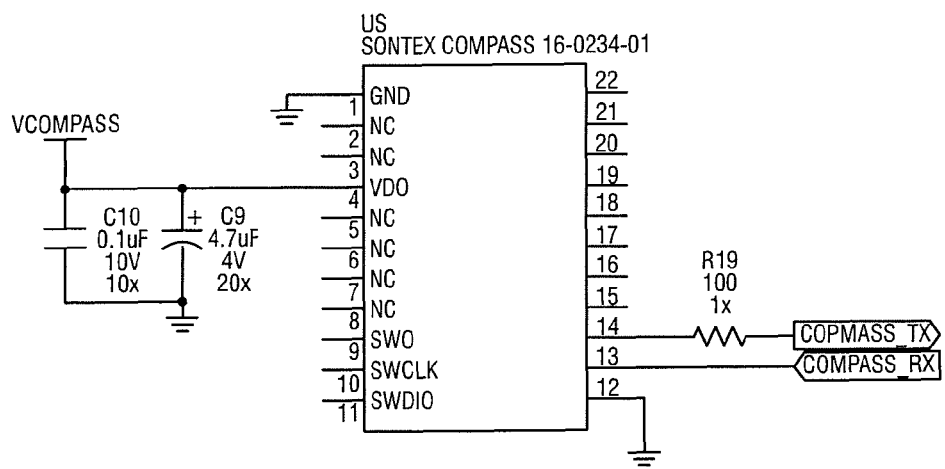
Figure 18A:
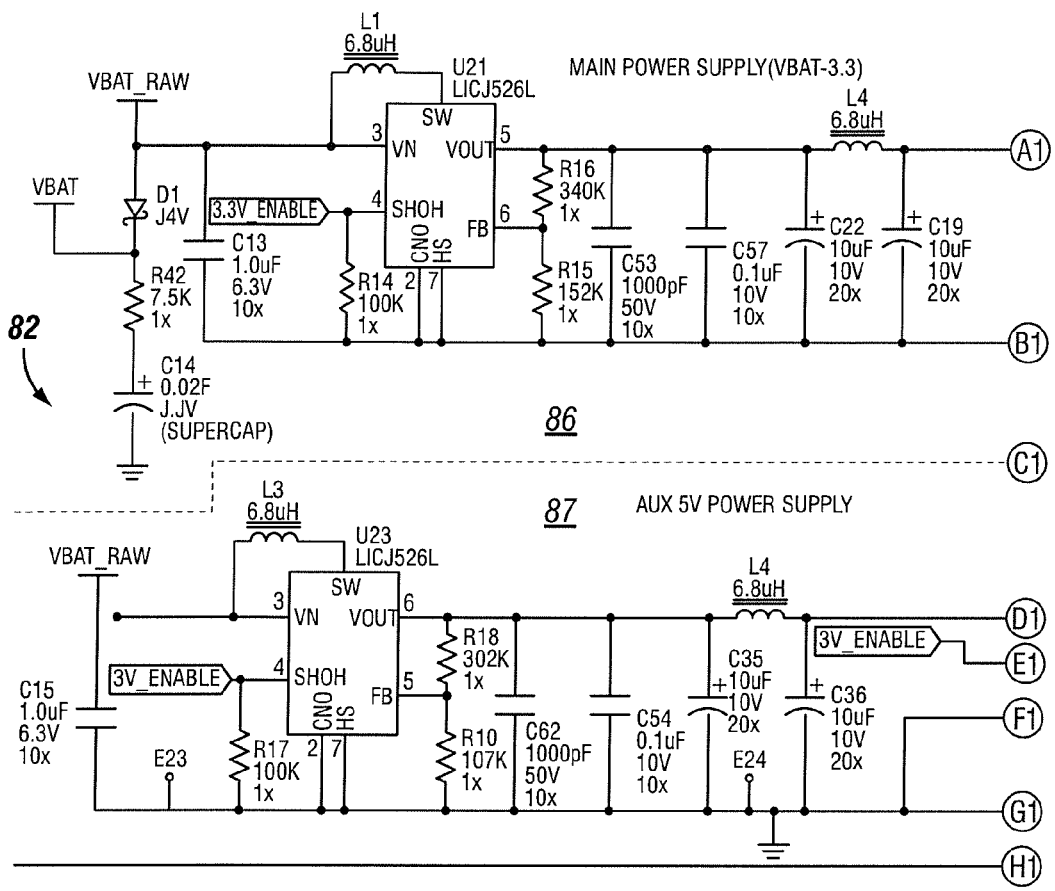
FIG. 18A is part one of a circuit diagram of a portion of a sensor board including a main power supply, an auxiliary power supply, and a CPU of an embodiment of an underwater sensor apparatus in accordance with the present disclosure.
Figure 18A:
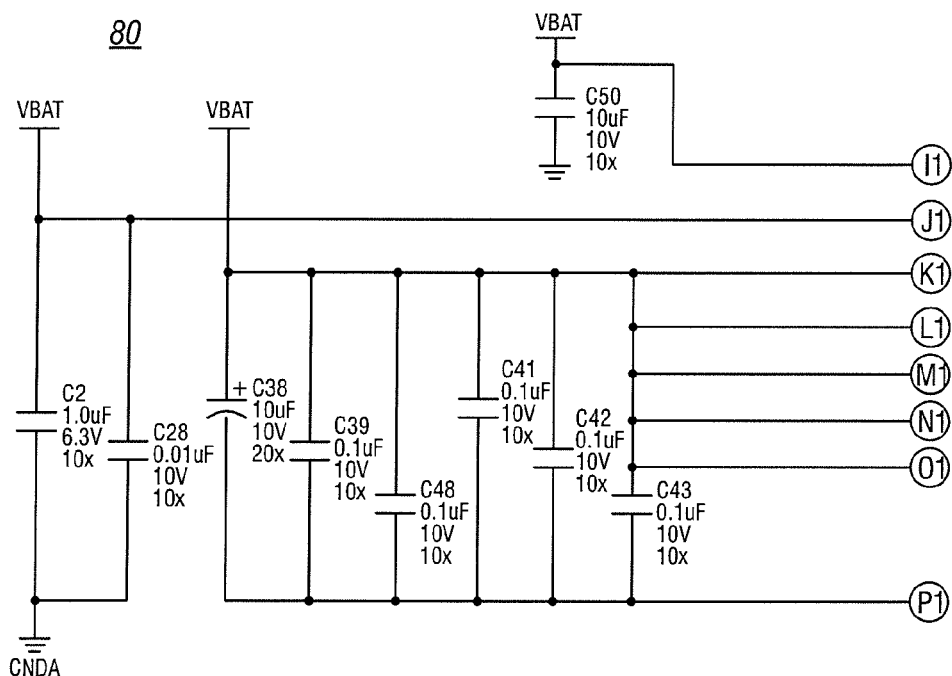
Figure 18B:
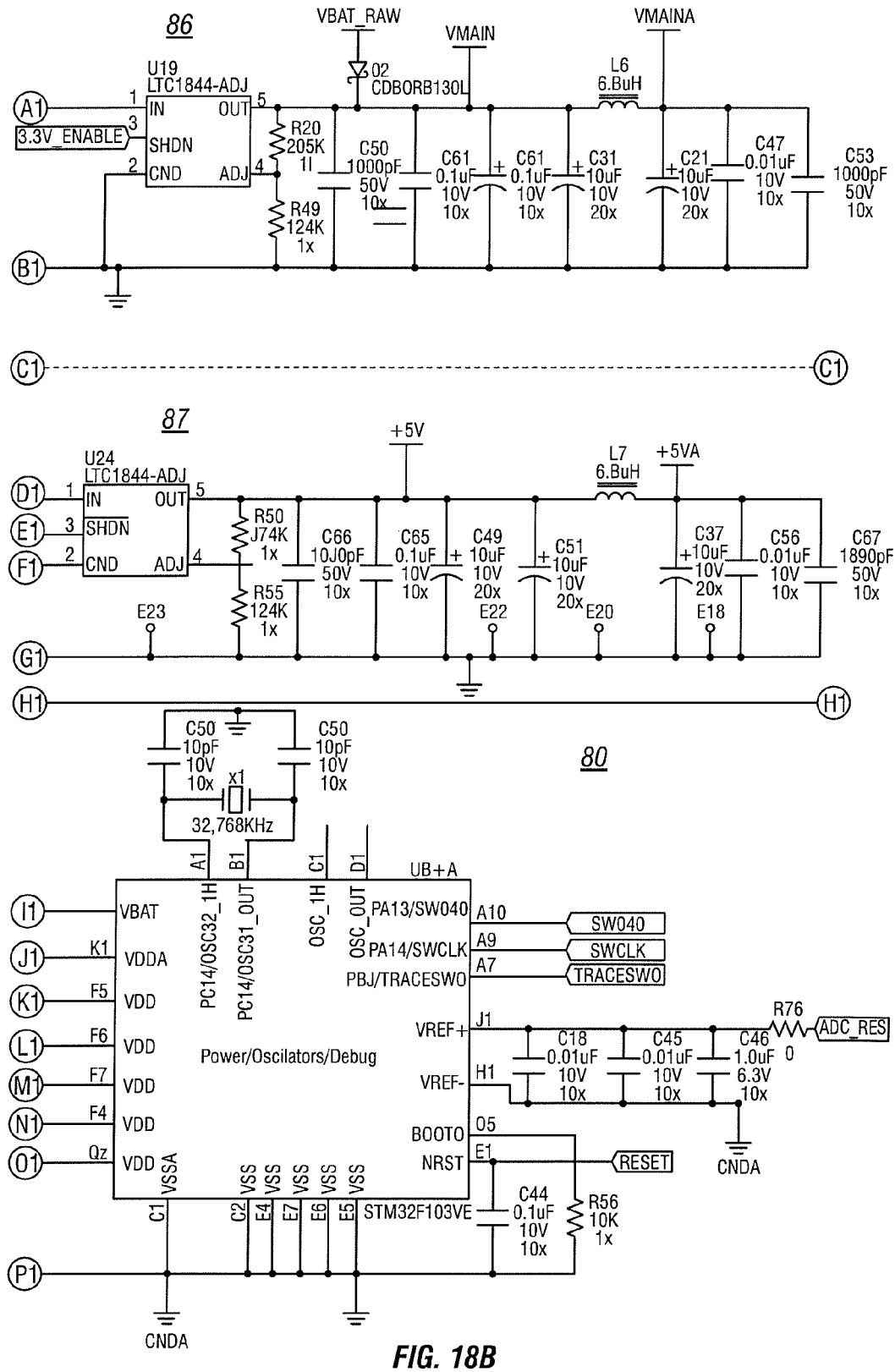
FIG. 18B is part two of a circuit diagram of a portion of a sensor board including a main power supply, an auxiliary power supply, and a CPU of an embodiment of an underwater sensor apparatus in accordance with the present disclosure.
Figure 18C:
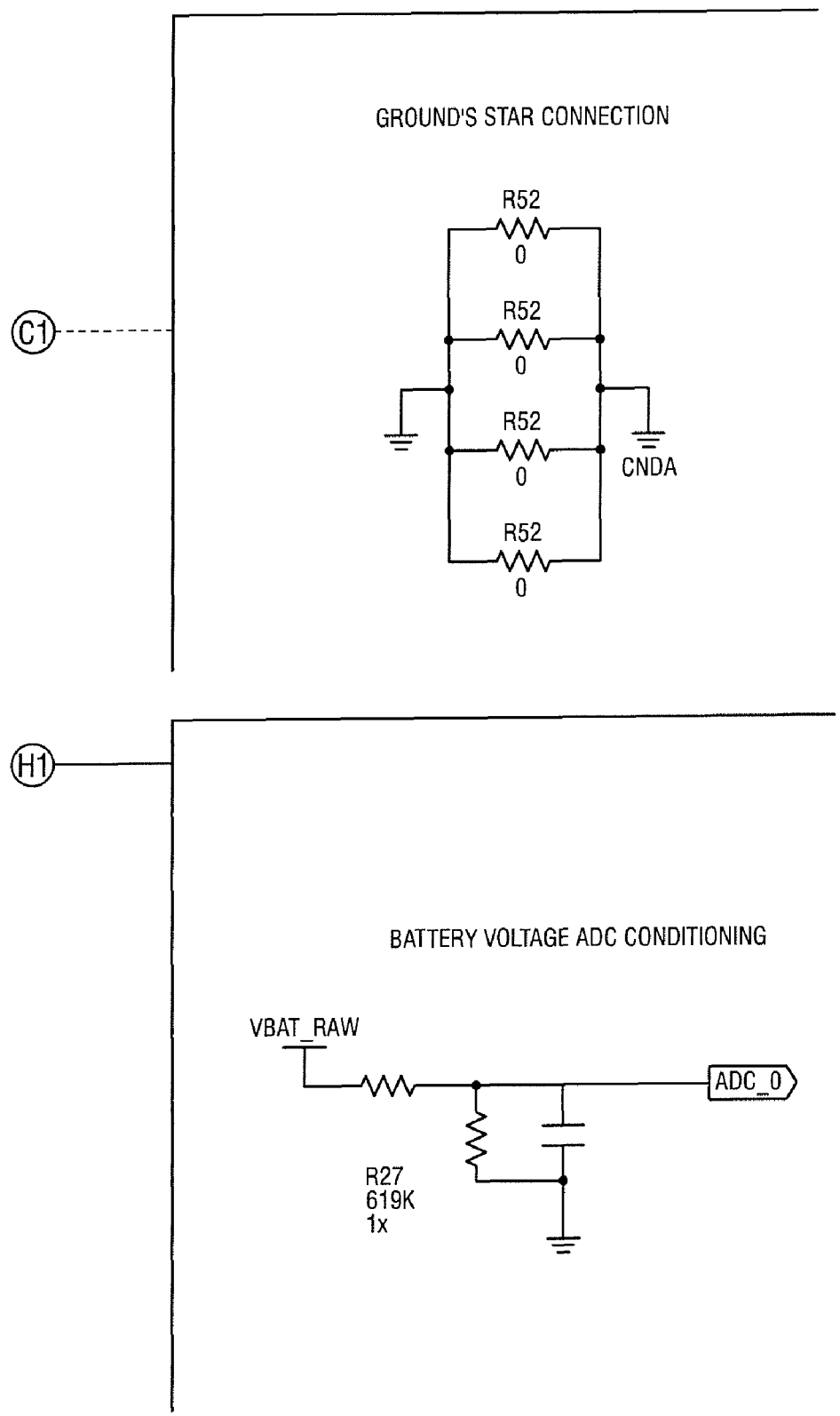
FIG. 18C is part three of a circuit diagram of a portion of a sensor board including a main power supply, an auxiliary power supply, and a CPU of an embodiment of an underwater sensor apparatus in accordance with the present disclosure.

FIGS. 14A-B and 16A-18C are system block and circuit diagrams that show the electrical connections of various sections of the underwater sensor apparatus. More particularly, FIGS. 14A-B is a system block diagram showing an overview of the electrical connections of an embodiment of an underwater sensor apparatus. FIGS. 16A-C is a schematic circuit diagram showing a portion of sensor board 82. FIGS. 17A-C is a schematic circuit diagram showing interface board 84. FIGS. 18A-C is a schematic circuit diagram showing another portion of sensor board 82 including main power supply 86, auxiliary power supply 87 and CPU 80.

Figure 9:
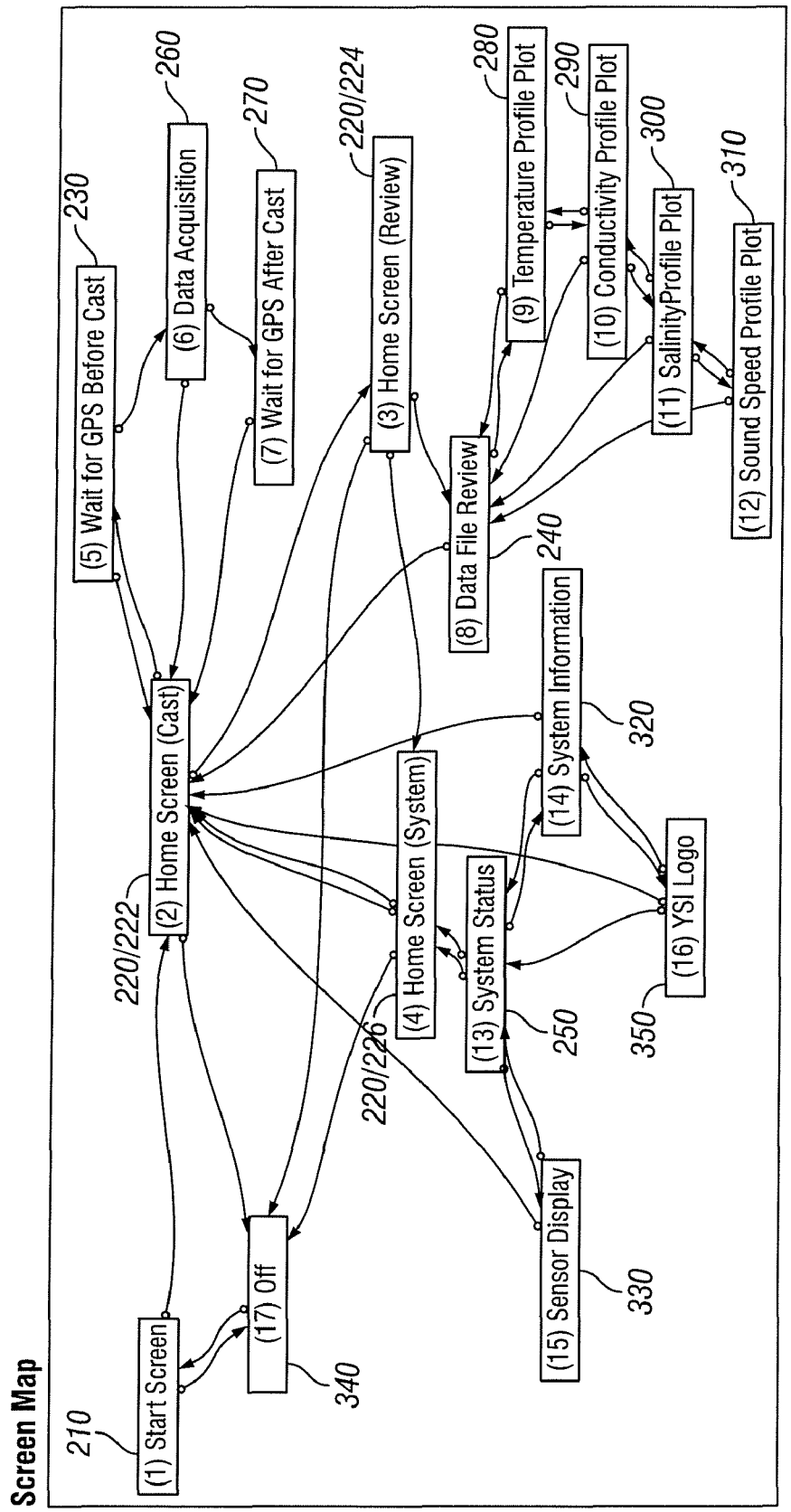
FIG. 9 is a flow diagram of a sequence of display screens of an underwater sensor apparatus in accordance with the present disclosure.

With reference to FIGS. 9-13, embodiments of an display 16 and its operation will now be described in more detail. The display 16 can display icons and/or text to guide the user through the operating system. FIG. 9 is a flow chart showing some of the different paths the user can take to view different screens on the display. Each screen is designed for a specific system function. When the underwater sensor apparatus 10 is turned on, as described above, a start screen/logo screen 210 is displayed. Start screen 210 may display brand information such as words or designs showing the name of the manufacturer of the underwater sensor apparatus or a trademark associated with the product.

Figure 10:
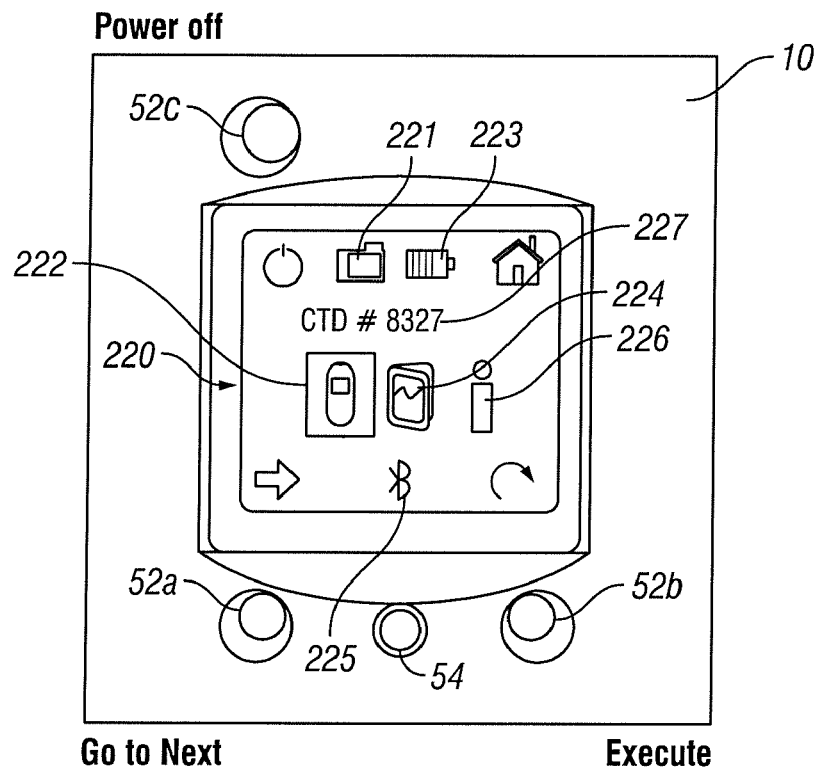
FIG. 10 is a detail view of an embodiment of an underwater sensor apparatus in accordance with the present disclosure showing an display screen.

The first screen with operational information on display 16 is home screen 220, which displays a menu of icons offering different functions. As shown in FIG. 10, in exemplary embodiments the menu of home screen 220 includes three branches and each branch is represented by an icon on the display screen. The first branch is a data collection branch that activates the GPS and starts data collection. The icon representing the data collection branch may be referred to as the "Cast" icon 222. The second branch, represented by the "Review" icon 224, provides a pathway to review collected data and displays the data in both text and graph form. The third branch is a system information branch having a system icon 226, which may be represented by a letter "i" and displays information about the underwater sensor apparatus. Home screen 220 may also include various other icons to indicate parameters such as a recorder status indicator 221 showing how full the recorder is with data, a battery life indicator 223, a Bluetooth indicator 225 showing whether Bluetooth is on or off, and the system serial number 227 and to provide the ability to move to other screens. A "House" icon indicates that the user is on the home screen 220.

Typical use would include first activating the GPS and data collection using the Cast icon 222 and then viewing the collected data using the Review icon 224. When the desired icon is selected, pressing the "execute" button 52b will activate the command associated with the selected icon. Pushing the "execute" button 52b with the cast icon 222 selected will activate a "Wait for GPS Before Cast" screen 230. Pushing the "execute" button 52b with the review icon 224 selected will activate a Data File review screen 240, and pushing the "execute" button 52b with the system icon 226 selected will activate a System Status screen 250. Each of these screens are discussed in turn below.

The "Wait for GPS Before Cast" screen 230 allows the user to prepare the system for cast or deployment by displaying real-time data from the GPS for determining the accuracy of the displayed location. The Wait for GPS Before Cast screen 230 may show the date and time and GPS position information in the form of latitude and longitude numbers. In exemplary embodiments, a circle icon (not shown) may change color with different colors indicating the quality of the location or GPS position. For example, a green light may indicate a good GPS position, a red light may indicate no GPS position, and a yellow light may indicate a satisfactory GPS position. A GPS quality indicator may also include varying numbers of bars of varying lengths. The user pushes button 52b to record the GPS location before casting the underwater sensor apparatus 10, and the button 52b is pressed again to start collecting data such as conductivity, temperature and pressure.

Figure 11:
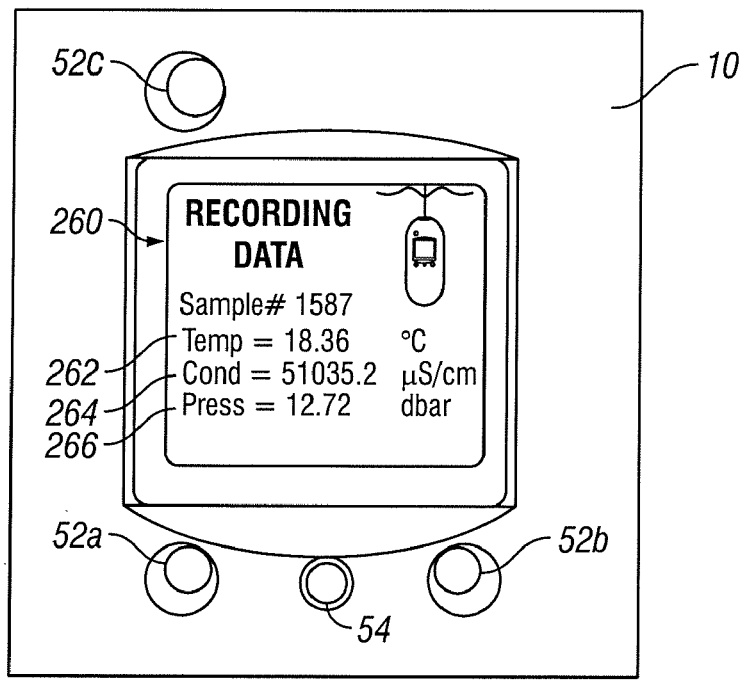
FIG. 11 is a detail view of an embodiment of an underwater sensor apparatus in accordance with the present disclosure showing an display screen.

The underwater sensor apparatus 10 is then ready for deployment and a Data Acquisition screen 260 is displayed. This screen indicates that data is being recorded onboard the underwater sensor apparatus 10. As shown in FIG. 11, the Data Acquisition screen 260 shows temperature, conductivity and pressure readings beneath large letters indicating that the device is recording data. At this point, the underwater sensor apparatus 10 may be secured with a line and tossed into the water. In exemplary embodiments, the screen is dimmable and may dim after deployment to conserve power. The underwater sensor apparatus 10 will measure and record data as it descends through the water, including, for example temperature data 262, conductivity data 264, sound speed data, salinity data, and pressure data 266. It should be noted that parameters such as temperature and conductivity are measured while parameters such as salinity and sound speed are typically calculated using oceanographic formulas. Once the device has reached the bottom of the body of water, it can be pulled back up using the attached line, and it will continue measuring and recording data as it ascends back up to the surface of the water. Upon retrieval of the underwater sensor apparatus 10, the user may push any button to activate the display and then push any button a second time to end the cast, close the data file, and start the GPS.

A second GPS location is then recorded at the end of the cast. This is particularly advantageous where the underwater sensor apparatus 10 has been cast from a moving boat. A "Wait for GPS after Cast" screen 270 appears next. This screen is similar to the Wait for GPS Before Cast screen 230 described above in that it displays location information such as latitude and longitude numbers, and indicates GPS signal quality by, e.g., a varying number and length of signal strength bars. The user pushes button 52b after the cast to record the location and can decide whether or not to wait for a good GPS position. As discussed above, a color-coded indicator uses green, yellow and red to indicate the quality of the GPS position. Pushing button 52a from this screen will return the user to Home Screen 220.

Data File review screen 240 appears when the user selects the review icon 224 and pushes button 52b. As shown in FIG. 12, the Data File review screen 240 displays the most recent data from the device's recorder. In exemplary embodiments, the data collected by the device's sensors are stored every 0.2 seconds (5 Hz). This screen also may indicate the start time and location of the cast, including the latitude 242 and longitude 244 displayed in decimal degrees, as well as the maximum depth 246 the device reached during the cast. When the Data File review screen 240 is accessed from the home screen 220, the most recent data on the recorder is displayed. The user can access older data files by using button 52a. Pressing button 52b will advance the user to the Temperature Profile screen 280.

In exemplary embodiments, a Temperature Profile screen 280 provides information relating to the temperature of the water being measured. This may include a graph that can show various parameters including a plot of temperature versus depth with the temperature statistics typically displayed in degrees Celsius, as well as the minimum, maximum and average temperature. The line on the graph may plot the average of the cast temperature measurements taken at each depth, including those taken during both the ascent and descent of the underwater sensor apparatus 10. In exemplary embodiments, the depth shown on the Temperature Profile screen is the extent of the plot of the graph, but could be other depths such as the maximum depth of the cast. The user can advance to a Conductivity Profile screen 290 by pressing button 52b.

Referring to FIG. 13, a Conductivity Profile screen 290 will be described. In exemplary embodiments, a Conductivity Profile screen 290 provides information relating to the conductivity of the water being measured. The information may include a graph 292 that plots conductivity versus depth with the conductivity statistics displayed in microSiemens per centimeter, as well as the minimum, maximum and average conductivity. In exemplary embodiments, the depth shown on the Conductivity Profile screen 290 is the extent of the plot of the graph, but could be other depths such as the maximum depth of the cast. The line on the graph may plot the minimum 291, maximum 293, and average 294 of the cast conductivity measurements taken at each depth, including those taken during both the ascent and descent of the underwater sensor apparatus 10. By pushing button 52b, the user can proceed to Salinity Profile screen 300.

The Salinity Profile screen 300 may provide salinity information including statistics displayed in parts per thousand. The salinity information may also include a graph that plots salinity versus depth. The line on the graph may plot the average of the cast salinity measurements taken at each depth, including those taken during both the ascent and descent of the underwater sensor apparatus 10. In exemplary embodiments, the depth shown on the Salinity Profile screen 300 is the extent of the plot of the graph, but could be other depths such as the maximum depth of the cast. Pressing button 52a will load the previous data file, and pressing button 52b will advance to the Sound Speed Profile screen 310.

The Sound Speed Profile screen 310 provides sound speed statistics, typically displayed in meters per second and including the average, minimum and maximum sound speed measured. The sound speed information may be presented in graph form with the plot line showing the average of the cast sound speed measurements taken at each depth, including those taken during both the ascent and descent of the underwater sensor apparatus 10. The depth shown on the Sound Speed Profile screen 310 is typically the extent of the plot of the graph, but could be other depths such as the maximum depth of the cast. The user can load the previous data file by pushing button 52 and can advance to the File Review screen 310 by pushing button 52b.

The System Status screen 250 displays basic information about the underwater sensor apparatus as well as date and time information. In exemplary embodiments, the date and time are shown in Coordinated Universal Time (UTC), also known as Greenwich Mean Time (GMT) or Zulu time. The underwater sensor apparatus periodically receives a correct time from the onboard GPS and updates the date and time. A Battery Health indicator displays the percentage of battery life remaining, and a Recorder Available indicator displays the percentage of data recorder space remaining. Exemplary embodiments may also include the date and time the underwater sensor apparatus was last used. A System Information screen 320 can be viewed by pressing button 52b and may provide general information such as the interne url and contact information for the manufacturer of the device, a phone number for customer service, and other information about the device system and software. Pressing button 52b from the System Information screen 320 will take the user to a TSI Logo screen 350.

From the System Status screen 250, pressing button 52a will take the user to the Sensor Display screen 330. Sensor Display screen 330 provides a real time display for a sensor status check and the point measurements for the different parameters such as temperature, conductivity and pressure without recording the data to the system. Finally, when the user is finished, the underwater sensor apparatus 10 may be powered off by pressing button 52c. This leads to a blank Off screen 340. From the Off screen 340, the user can go to the Start screen 210 by pressing any of buttons 52a, 52b or 52c.

While embodiments of the disclosure have been described above, it will be apparent to one skilled in the art that various changes and modifications may be made. It should be understood that any of the foregoing configurations and specialized components may be interchangeably used with any of the systems of the preceding embodiments. Although illustrative embodiments are described hereinabove, it will be evident to one skilled in the art that various changes and modifications may be made therein without departing from the invention. It is intended in the appended claims to cover all such changes and modifications that fall within the true spirit and scope of the invention.

The invention claimed is:

1. An apparatus for monitoring and collecting water environmental data, comprising:
   a submersible housing;
   one or more sensors for collecting selected water environmental data, the sensors being mounted to the housing;
   a controller for controlling operations of the one or more sensors, the controller being disposed within the housing and operatively connected to the one or more sensors; and
   an graphical user interface mounted to the housing that displays the water environmental data;
   a GPS receiver disposed within the housing; and
   a transceiver disposed within the housing for sending the water environmental data to a remote data collection system.

2. The apparatus of claim 1 wherein the channel defines one or more access points and one or more of the sensors extend into the channel through the access points.

3. The apparatus of claim 1 further comprising a channel that has a first end and a second end and each end is substantially funnel-shaped.

4. The apparatus of claim 1 further comprising a jacket covering the submersible housing.

5. The apparatus of claim 1 wherein the GPS collects geographical data and sends at least some of the geographical data through the transceiver to a remote data collection system.

6. The apparatus of claim 1 wherein the submersible housing defines a channel extending therethrough, the channel being oriented such that water flows through the channel when the system is submerged and moving.

7. The apparatus of claim 6 wherein the submersible housing comprises two housing components such that the first housing component houses the graphical user interface and the second housing component houses the one or more sensors.

8. The apparatus of claim 7 further comprising an interface module providing an electrical interconnection between the sensors and the graphical user interface.

9. The apparatus of claim 6 wherein the channel is defined in the second housing component.

10. The apparatus of claim 1 further comprising a weighted endcap component fixedly attached to the submersible housing at a bottom portion thereof.

11. The apparatus of claim 1 wherein the sensors include one or more of: a temperature sensor, a conductivity electrode and a pressure sensor.

12. The apparatus of claim 1 further comprising a pressure cal module operatively connecting the one or more sensors to the controller.

13. The apparatus of claim 1 further comprising a stylus and one or more magnetic switches activated by the stylus.

14. A sensor apparatus comprising:
a submersible housing including a first and second housing component, the second housing component defining a channel extending therethrough;
an endcap component fixedly attached to the one or more housing components at a bottom portion thereof;
one or more sensors for monitoring and collecting water environmental data, the sensors being mounted to the second housing component;
an display mounted to the first housing component that displays the water environmental data; and
an interface module located between the one or more sensors and the display and electrically connecting the one or more sensors to the display.

15. The sensor apparatus of claim 14 wherein the channel defines one or more access points and the one or more sensors extend into the channel through the access points.

16. The sensor apparatus of claim 14 wherein the endcap component is weighted to maintain the sensor apparatus in an orientation substantially vertical when being lowered or raised in water.

17. The sensor apparatus of claim 14 further comprising a controller for controlling operations of the one or more sensors, the controller being disposed within the housing and operatively connected to the one or more sensors.

18. The sensor apparatus of claim 14 further comprising a GPS receiver adapted to collect geographical data, the GPS receiver being disposed within the housing.

19. The sensor apparatus of claim 14 further comprising a transceiver disposed within the housing, the transceiver sending the water environmental data to a remote data collection system.

20. An underwater sensor device comprising:
a submersible housing including one or more housing components, the housing defining a channel that extends through one of the housing components;
one or more sensors for monitoring and collecting environmental data, at least one of the sensors being mounted to the housing and extending into the channel;
a controller for controlling operations of the one or more sensors, the controller being disposed within the housing and operatively connected to the one or more sensors; and
an graphical user interface mounted to the housing that displays the environmental data.

* * * * *